US008680051B2

(12) United States Patent
Wang et al.

(10) Patent No.: US 8,680,051 B2
(45) Date of Patent: Mar. 25, 2014

(54) METHOD OF AMELIORATING SYMPTOMS OF TYPE 1-DIABETES USING GABA RELATED COMPOUNDS AND GLP-1/EXENDIN-4 COMPOUNDS

(75) Inventors: Qinghua Wang, Toronto (CA); Soltani Nepton, Thornhill (CA)

(73) Assignee: Qinghua Wang, North York (CA)

( * ) Notice: Subject to any disclaimer, the term of this patent is extended or adjusted under 35 U.S.C. 154(b) by 488 days.

(21) Appl. No.: 12/643,008

(22) Filed: Dec. 21, 2009

(65) Prior Publication Data

US 2010/0166675 A1 Jul. 1, 2010

Related U.S. Application Data

(60) Provisional application No. 61/138,957, filed on Dec. 19, 2008.

(51) Int. Cl.
*A61K 38/00* (2006.01)
*C12P 41/00* (2006.01)
*C12P 13/00* (2006.01)

(52) U.S. Cl.
USPC ............... 514/7.3; 514/6.8; 514/6.9; 514/7.2; 514/546; 514/561

(58) Field of Classification Search
None
See application file for complete search history.

(56) References Cited

U.S. PATENT DOCUMENTS

| 5,424,286 | A | * | 6/1995 | Eng ................................. 514/5.9 |
| 7,423,169 | B2 | | 9/2008 | Raillard et al. |
| 2003/0162754 | A1 | * | 8/2003 | Ligon ........................... 514/114 |

OTHER PUBLICATIONS

Zhang, 2007, Diabetologica, vol. 50, pp. 1900-1909.*
Bansal, P. et al., "Insulin as a Physiological Modulator of Glucagon Secretion", American Journal of Physiology-Endocrinology & Metabolism, 2008, pp. E751-E761, vol. 295(4).
Franklin, I.K. et al., "GABA in the Endocrine Pancreas: Its Putative Role as an Islet Cell Paracrine . . . ", Journal General Physiology, 2004, pp. 185-190, vol. 123, Issue 3.
Rorsman, P. et al., "Glucose-Inhibition of Glucagon Secretion Involves Activation of GABAA-Receptor Chloride Channels", Nature, 1989, pp. 233-236, vol. 341(6239).
Xu, E. et al., "Intra-islet Insulin Suppresses Glucagon Release via GABA-GABAA Receptor System", Cell Metabolism, 2006, pp. 47-58, vol. 3, Issue 1.
Murphy, K.D. et al., "The Effects of Gammahydroxybutyrate on Hypermetabolism and Wound Healing in a Rat Model . . . ", Journal of Trauma., 2007, pp. 1099-1107, vol. 63, Issue 5.
Dong, H. et al., "Gamma-Aminobutyric Acid Up- and Down Regulates Insulin Secretion from Beta Cells in Concert . . . ", Diabetologia, 2006, pp. 697-705, vol. 49, No. 4.
Ligon, B. et al., "Regulation of Pancreatic Islet Cell Survival and Replication by γ-Aminobutyric Acid", Diabetologia, 2007, pp. 764-773, vol. 50, No. 4.
Alam, S. et al., "Human Peripheral Blood Mononuclear Cells Express GABAA Receptor Subunits", Molecular Immunology, 2006, pp. 1432-1442, vol. 43, Issue 9.
Tian, J. et al., "GABA(A) Receptors Mediate Inhibition of T Cell Responses", Journal of Neuroimmunology, 1999, pp. 21-28, vol. 96, Issue 1.
Tian, J. et al., "Gamma-aminobutyric Acid Inhibits T Cell Autoimmunity and the Development of Inflammatory Responses . . . ", Journal of Immunology, 2004, pp. 5298-5304, vol. 173.
Nakagawa, T. et al., "Protective Effects of γ-Aminobutyric Acid in Rats with . . . ", Journal of Nutritional Science and Vitaminology, 2005, pp. 278-282, vol. 51, Issue 4.
Foster, Alan C. et al. Glutamane- and GABA-based CNS therapeutics. Current Opinion in Pharmacology 2006, 6:7-17.
Frolund, B., et al., GABA(A) receptor ligands and their therapeutic potentials. Curr Top Med Chem. Aug. 2002;2 (8):817-32. Abstract.
Gallwitz B., et al. GLP-1-analogues resistant to degradation by dipeptidyl-peptidase IV in vitro. Regul Pept. Jan. 29, 2000;86_1-3):103-11. Abstract.
Green, B. D. et al. Novel dipeptidyl peptidase IV resistant analogues of glucagon-like peptide-1(7-36)amide have preserved biological activities in vitro conferring improved glucose-lowering action in vivo. Journal of Molecular Endocrinology (2003) 31, 529-540.
Hadjiyanni, Irene et al. Exendin-4 Modulates Diabetes Onset in Nonobese Diabetic Mice. Endocrinology 149 (3):1338-1349.
Juhl B. Claus et al. Bedtime Administration of NN2211, a Long-Acting GLP-1 Derivative, Substantially Reduces Fasting and Postprandial Glycemia in Type 2 Diabetes. Diabetes, vol. 51 Feb. 2002 pp. 424-429.
Liu, Hui-Kang et al. N-acetyl-GLP-1: a DPP IV-resistant analogue of glucagon-like peptide-1 (GLP-1) with improved effects on pancreatic B-cell-associated gene expression. Cell Biology International 28 (2004) 69-73.
Wu, Heng et al. Role of glutamate decarboxylase (GAD) isoform, GAD65, in GABA synthesis and transport into synaptic vesicles-Evidence from GAD65-knockout mice studies. Brain Research 1154 (2007) 80-83.
Zwanzger, Peter et al. Selective GABAergic treatment for panic? Investigations in experimental panic induction and panic disorder. J Psychiatry Neuroscience 2005; 30(3) pp. 167-175.
D'Alessio David A. et al. Glucagon-like peptide 1: evolution of an incretin into a treatment for diabetes. Am J Physiol Endocrinology and Metabolism 286:E882-E890, 2004.
Youngblood, WW., et al. Bovine serum albumin-GABA-His-Pro-NH2: an immunogen for production of higher affinity antisera for TRH. J Neurosci Methods. Dec. 1983;9(4):367-73. Abstract.

(Continued)

*Primary Examiner* — Joanne Hama
*Assistant Examiner* — Ian Dang
(74) *Attorney, Agent, or Firm* — Bereskin & Parr LLP; Camela DeLuca

(57) ABSTRACT

A composition for the prevention or treatment of type I diabetes in a subject, said composition comprising a GABAergic and incretin exemplified by GABA and GLP-1/Ex4. These are optionally provided together in a single composition to promote beta-cell regeneration prevent beta-cell apoptosis and control autoimmunity for the prevention and treatment of T1D in mammals.

4 Claims, 16 Drawing Sheets

(56) References Cited

OTHER PUBLICATIONS

Carelli, Vicenzo et al. Synthesis and Biological Evaluation of GABA Derivatives Able to Cross the Blood-Brain Barrier in Rats. Bioorganic & Medicinal Chemistry Letters 13 (2003) 3764-3769.

Tominaga Keido et al. GABAa receptor agonist muscimol can reset the phase of neural activity rhythm in the rat suprachiasmatic nucleus in vitro. Neuroscience Letters. 166 (1994) 81-84.

GABAergic. In TheFreeDictionary. Retrieved Feb. 2012, from http://medical-dictionary.thefreedictionary.com/GABAergic.

Gamma-Aminobutyric acid. In Wikipedia. Retrieved Feb. 2012, from http://en.wikipedia.org/wiki/GABAergic#GABAergic_Drugs.

Hadjiyanni, Irene et al. Exendin-4 Modulates Diabetes Onset in Nonobese Diabetic Mice. Endocrinology 149 (3):1338-1349, 2008.

* cited by examiner

METHOD OF AMELIORATING SYMPTOMS OF TYPE 1-DIABETES USING GABA RELATED COMPOUNDS AND GLP-1/EXENDIN-4 COMPOUNDS

RELATED APPLICATIONS

This application claims the benefit of 35 USC 119 based on the priority of U.S. Provisional Patent Application 61/138,957, filed Dec. 19, 2008 which is incorporated herein in its entirety by reference.

FIELD

The invention provides compositions and methods for the prevention and treatment of diabetes. In particular, the invention provides a composition and method for the prevention and treatment of type 1 diabetes (T1D) in a subject in need thereof. The composition comprises gamma-aminobutyric acid (GABA), or GABAergic alone or in combination with incretins, in particular glucagon-like peptide-1 (GLP-1) and its mimetics that promote islet beta-cell regeneration, prevent beta-cell apoptosis, suppress inflammation, decrease islet beta-cell autoimmunity and enhance regulatory T-cell functions.

BACKGROUND OF THE INVENTION

Diabetes is one of the leading causes of death by disease worldwide. T1D, is a major form of the disease that typically develops at a young age and results from autoimmune destruction of islet beta-cells with consequent insulin deficiency and dependence on exogenous insulin treatment. Apoptosis is the main type of beta-cell death of in T1D. Under normal conditions, maintenance of beta-cell mass is a dynamic process, undergoing both increases and decreases which is dependent on the rates of beta cell survival (i.e. beta-cell proliferation and neogenesis) and beta-cell death (i.e. beta-cell apoptosis and necrosis) thereby control body glucose levels within a narrow physiological range (Bonner-Weir S 2000 Trends Endocrinol Metab, 11:375-378; Bonner-Weir S 2000 Endocrinology 141:1926-1929. In subjects with type 1 diabetes the islet beta-cells are persistently insulted by autoimmune destruction. The beta-cell apoptosis occurs as a result of autoimmune destruction involving T cell infiltration of the islets of Langerhans (Mandrup-Poulsen T 2003 Biochem Pharmacol 66:1433-1440; Mathis D et al, 2001 Nature 414:792-798; Sesti G 2002 Ann Med 34:444-450). The progressive destruction of the pancreatic beta-cells is largely due to lymphocytic infiltration of the islet, resulting in insulin deficiency. Inflammatory cytokines including IL-1beta, TNF-alpha and IFN-gamma are released by macrophages and T cells during this autoimmune response and are important mediators of beta-cell destruction (Mandrup-Poulsen T 2003 Biochem Pharmacol 66:1433-1440; Eizirik D L, Mandrup-Poulsen T 2001 Diabetologia 44:2115-2133; Saldeen J 2000 Endocrinology 141:2003-2010). In the early stage of disease, a compensatory mechanism by which the islet beta-cells attempt expanding to overcome the beta-cell damage caused by autoimmune attack, play a role in maintenance of body's blood glucose. When the rate of beta-cell death significantly exceeds the rate of beta-cell growth, the beta-cells mass is significantly decreased leading to insulin insufficiency and development of diabetic hyperglycemia. Insulin therapy is the major intervention for the treatment of type I diabetes, however, insulin is not a cure as it is hard to manage the exogenous insulin to meet body's needs in a glucose-sensing manner thus to maintain blood glucose levels within a narrow physiological range. Exogenous insulin does not prevent the progression of the disease and severe diabetic complications that eventually arise. Pancreatic islet transplantation is also an effective therapy (Shapiro A M et al, 2000 N Engl J Med 343:230-238) but is limited largely by the limited resources of human islets. In addition, immune-suppressors need to be used for life in the islets-transplanted patients.

At the onset of T1D, over 70-80% of beta-cells have been destroyed (Cnop M et al, 2005 Diabetes 54 Suppl 2:S97-107). The multiple low dose streptozotocin (MLDS) murine model of diabetes is characterized by a progressive hyperglycemia and T-cell mediated beta-cell inflammation (insulitis) similar to that observed in human subjects with recent onset T1D (Rossini A A et al, 1978 Nature. 276(5684):182-4; Harlan D M et al, 1995 Diabetes 44(7):816-23). Another animal model is the non-obese diabetic (NOD) mouse. These mice are an excellent model of autoimmune diabetes (type I diabetes) where islet-antigen reactive T cells infiltrate islets of Langerhans and kill islet beta-cells, and/or initiate an inflammatory process that results in islet beta-cell death (Anderson M S and Bluestone J A 2005 Annu Rev Immunol. 23:447-85). NOD mouse develops spontaneous autoimmune diabetes that shares histoimmunological, serological and clinical features with T1D in humans (Tisch R, McDevitt H. 1996 Cell 85(3):291-7; Atkinson M A, Leiter E H. Nat Med. 5(6):601-4). These mice have thus been used extensively and are recognized as the animal model that are mimics type I diabetes in subjects.

Incretins are gastrointestinal hormones that play important role in maintaining body blood glucose levels. The important incretin hormones are glucagon-like peptide-1 (GLP-1) and gastric inhibitory peptide (glucose-dependent insulinotropic peptide or GIP) (Brubaker P L, Drucker D J 2004 Endocrinology 145:2653-2659). Given GLP-1 as an example, this hormonal peptide is secreted from the enteroendocrine L cells of the intestinal tract in response to nutrient ingestion (Hoist J J 1994 Gastroenterology 107:1848-1855; Perfetti R, Merkel P 2000 Eur J Endocrinol 143:717-725). Importantly, GLP-1 is also found to be produced in the islet alpha-cells (Jin T. J 2008 Endocrinol. 198(1):17-28). GLP-1 enhances pancreatic islet beta-cell neogenesis/proliferation and inhibits beta-cell apoptosis; in a glucose-dependent fashion (Nauck M A 2004 Horm Metab Res 36:852-858; Drucker D J 2001 Endocrinology 142:521-527). GLP-1 also augments insulin secretion and lowers blood glucose in rodents as well as in humans in both type I diabetes (17;18) and type II diabetes Gutniak M et al, 1992 N Engl J Med 326:1316-1322; Dupre J et al J Clin Endocrinol Metab 89:3469-3473). Previous studies have demonstrated that in insulin-secreting beta-cells, the apoptosis and necrosis induced by cytokines could be significantly improved by glucagon-like peptide-1 (GLP-1) or Ex4, a long-acting potent agonist of the GLP-1 receptor (Saldeen J 2000 Endocrinology 141:2003-2010; Li L et al, Diabetologia 48(7):1339-49). In vivo studies have shown that treatment with GLP-1/Ex4, stimulated beta-cell neogenesis in streptozotocin (STZ)-treated newborn rats resulting in persistently improved glucose homeostasis at an adult age (Tourrel C et al, 2001 Diabetes 50:1562-1570). In type I diabetes patients, treatment with Ex4 improved postcibal glycemic excursions (Dupre J et al, 2004 J Clin Endocrinol Metab 89:3469-3473). It is believed that the mechanism by which GLP-1 modulates beta-cell mass involves primarily 1) enhancement of β-cell proliferation, 2) inhibition of apoptosis of β-cells and 3) beta-cell neogenesis (Brubaker P L, Drucker D J 2004 Endocrinology 145:2653-2659).

The biological actions of GLP-1 exert through the activation of the GLP-1 receptor, (GLP-1R). GLP-1R is a member of G-protein coupled receptor (GPCR) superfamily that are expressed mainly by pancreatic beta-cells and to some extent by cells of other tissues (lungs, heart, kidney, GI tract and brain), and is coupled to the cyclic AMP (cAMP) second messenger pathway (Brubaker P L, Drucker D J 2004 Endocrinology 145:2653-2659; Drucker D J 1998 Diabetes 47:159-169). Activation of other protein kinases including Akt (protein kinase B) (Wang Q et al Diabetologia 47:478-487; Brubaker P L, Drucker D J 2004 Endocrinology 145:2653-2659) is found to be important in mediating GLP-1 action in promoting beta-cell growth and inhibiting apoptosis. In animals models of type II diabetes, it has been recently demonstrated that treatment of GLP-1 or Ex4 prevented onset of diabetes (Wang Q, Brubaker P L 2002 Diabetologia 45:1263-1273; Tourrel C, et al, 2002 Diabetes 51:1443-1452) by enhancing beta-cell growth and inhibiting apoptosis (Wang Q, Brubaker P L 2002 Diabetologia 45:1263-1273; Wang Q et al, Diabetologia 47:478-487). GLP-1 has demonstrated clinical efficacy in type II diabetes (Meier J J, Nauck M A 2005 Diabetes Metab Res Rev 21:91-117). It has been demonstrated that expansion of beta-cell mass by treatment with glucagon-like peptide-1 (GLP-1) prevented the onset of diabetes in animal models predisposed to type II diabetes (Wang Q, Brubaker P L 2002 Diabetologia 45:1263-1273; Tourrel C et al, Diabetes 51:1443-1452). U.S. Pat. No. 6,899,883 and U.S. Pat. No. 6,989,148 disclose methods of treating type I diabetes using insulin and glucagon-like peptide 1(7-37) or glucagon-like peptide 1(7-36) amide.

Ex4 is peptide of 39 amino acids that has been isolated from the venom of the lizard Heloderma suspectum (Gila monster) (Eng J et al J Biol Chem. 1992 15; 267(11):7402-5). Ex4, a mammalian homolog does not seem to exist (Pohl M, Wank S A. 1998 J Biol Chem. 17; 273(16):9778-84.), shares 53% identity at the amino acid level with the mammalian hormone GLP-1 (Drucker D J 2001 Endocrinology 142:521-527). This peptide displays similar functional features to native GLP-1, including regulation of blood glucose homeostasis, Stimulation of insulin secretion and suppression of glucagon secretion. Ex4 also regulates gastric emptying, food intake. Previous studies showed that Ex4 decreased blood glucose in normal rodents and in animal models of type 2 diabetes (Raufman J P. 1996 Regul Pept. 61(1):1-18). Acting as an agonist of GLP-1 receptor, Ex4, commercially named as Exenatide or Byetta has been approved by the FDA on Apr. 28, 2005 for the treatment of type 2 diabetes.

Previous preclinical and clinical studies have showed that GLP-1 or its potent analogue is consistently effective in lowering blood glucose in type 2 diabetes animals and humans. However, GLP-1, is only marginally effective in T1D-prone NOD mice (Hadjiyanni I et al, Endocrinology. 2008 March; 149(3):1338-49). Although Ex4 administered before breakfast also reduced blood glucose in short term studies of human subjects with T1D, likely due to inhibition of glucagon and slowing of gastric emptying (Exendin-4 normalized postcibal glycemic excursions in T1D. (Dupré J, et al 2004 J Clin Endocrinol Metab. 89(7):3469-73). The effects of Ex4 on the prevention of the onset of type 1 animal diabetes appears modest. Study in NOD mice showed that sustained GLP-1R activation was found in the absence of concomitant immune intervention, which was associated only with a transient and modest delay in diabetes onset in these T1D murine models (Hadjiyanni I et al, 2008 Endocrinology 149(3):1338-49), suggesting that GLP-1 alone has very limited effects on the prevention of the development of T1D.

The loss of beta-cell mass in T1D is mainly due to specific autoimmune attack to the islet beta-cells. It is conceivable that a strategy involving promotion of beta-cell growth alone is neither sufficient to prevent the development of T1D nor to effectively treat established T1D in a subject.

Many forms of immunotherapy ameliorate diabetes in NOD mice (Anderson M S, Bluestone J A 2005 Annu Rev Immunol 23:447-485), although most are effective only if initiated prior to the onset of the disease. Unfortunately, most patients initially present with diabetes. More recently, CD3 monoclonal antibody (mAb) therapy was found effective after the onset of disease in NOD mice, and acts by inducing regulatory T cells (Tr) (Belghith M, 2003 Nat Med 9:1202-1208). However, recent clinical trials suggest that CD3 mAb therapy by itself delays beta-cell loss, but cannot return patients to normoglycemia (Herold K C, et al 2005 Diabetes 54:1763-1769). This is presumably because newly diabetic patients have a limited number of residual islet beta-cells, which are not sufficiently protected or replenished by this treatment. Another limitation is that most forms of immunotherapy (as in the case of CD3) are not specific to the auto-aggressive T cells, and affect many other immune responses, possibly causing undesirable effects. Notably, administration of ChAglyCD3 (a humanized CD3 mAb) was frequently associated with a cytokine release syndrome and transient Epstein-Barr viral mononucleosis (Keymeulen B et al, 2005 N Engl J Med 352:2598-2608). The failure in the previous clinical trails rationally by tolerizing autoreactive T-cells through administration of islet beta cell antigen (YU L P et al 2002 Ann. N.Y. Acad. Sci. 958: 254-258; Carel J 2002 Engl J Med; 347:1115-1116) suggest that such approaches using tolerizing T-cell alone either did not effectively delay or prevent T1D (Sia C, Homo-Delarche F 2004 Rev Diabet Stud. 1(4):198-206). The findings of these clinical trials using tolerizing autoreactive T-cell strategy also suggest that rather than tolerizing T-cell, the educating T-cell (i.e. suppressing diabetogenic T-cells and enhancing regulatory T-cells) may be of beneficial to maintain the balance of the autoimmune regulation. Therefore, a therapy using the beta-cell growth factor such as GLP-1/Ex4 and combined with an autoimmune suppressor is required to achieve appropriate therapeutic efficacy. In consistent to this notion, recent pre-clinical studies demonstrated that administration of GLP-1/Ex4, combined with immunosuppression by polyclonal anti-T cell antibody (Ogawa N, et al, 2004 Diabetes 53:1700-1705) or anti-CD3 antibody (Exendin-4 improves reversal of diabetes in NOD mice treated with anti-CD3 monoclonal antibody by enhancing recovery of beta-cells. Sherry N A et al 2007 Endocrinology 148(11):5136-44) induced remarkable remission of overtly diabetic NOD mice. However, obvious shortage of this strategy is that the systemic suppression of immunological responses by an anti-T-cell antibody or anti-CD3 antibody may lead to adverse immunologic effects (Keymeulen B, et al, 2005 N Engl J Med 352:2598-2608).

GABA is an important endogenous amino acid synthesized from glutamic acid by glutamate decarboxylase (GAD) (Gottlieb D I. 1988 Sci Am. 258(2):82-9). The role of GABA in the central nervous system has been extensively studied (Gramsbergen J B 2007 J Neurochem. 103(5):1697-708). GABA exerts its biological actions through the activation of its receptors. Three types of GABA receptor, type A, type B and type C ($GABA_{A-C}R$) are responsible to mediate GABA actions. GABA has long been considered to be the primary inhibitory neurotransmitter in the mammalian brain, and $GABA_AR$ is believed to mediate the main GABA inhibitory effects. Whereas under certain circumstance, the excitatory effects of GABA can be mediated by $GABA_AR$ (Gramsbergen J B 2007

J Neurochem. December; 103(5):1697-708). During brain development and neuronal maturation GABA acts as a trophic factor (Owens D F, Kriegstein A R. 2002 Nat Rev Neurosci. 3(9):715-27;) and modulates neuronal cell proliferation, migration and differentiation (Owens D F, Kriegstein A R. 2002 Nat Rev Neurosci. 3(9):715-27; LoTurco, J J et al, 1995 Neuron 15:1287-1298; Owens, D F et al, 1999 J. Neurophysiol. 82, 570-583).

In the pancreas, GABA is secreted from the islet beta-cells, acting as auto- or paracrine modulator via its receptors in both alpha- and beta-cells (Bansal P, Wang Q. 2008 Am J Physiol Endocrinol Metab. 295(4):E751-61; Franklin I K, Wollheim C B. 2004 Gen Physiol. March; 123(3):185-90). In particular, GABA suppresses glucagon secretion from alpha-cells through the activation of the $GABA_A$ receptor (Rorsman P et al Nature. 1989 341(6239):233-6; Xu E et al, 2006 Cell Metab. 3(1):47-58), while influences beta-cell metabolism and insulin secretion (Murphy K D et al, 2007 J Trauma. 63(5):1099-107; Dong H et al. 2006 Diabetologia 49(4):697-705). In vitro studies demonstrated that GABA promotes beta-cell proliferation inhibits apoptosis (Ligon B et al. 2007 Diabetologia 50(4):764-73). GABA improves metabolism through the modulation of endogenous growth hormones (Murphy K D et al, 2007 J Trauma. 63(5):1099-107). $GABA_AR$ are also expressed in T-lymphocytes which provides a fundamental base that GABA can exert direct effects on the T-cells (Alam et al., Mol Immunol, 2006, 43: 1432-42). GABA treatments inhibit the pro-inflammatory T cell response and halt the progression of T1DM in the NOD mouse animal model (Tian et al., 1999 J Neuroimmunol, 96: 21-28; and Tian et al., 2004 J. Immunol., 173:5298-304). In a rat model, GABA has protective effects on streptozotocin-induced diabetes (Nakagawa T, et al, 2005 J Nutr Sci Vitaminol (Tokyo). 51(4):278-82). However, there is no previous art demonstrating that GABA could reverse diabetes after onset of diabetes in a subject.

SUMMARY

Described herein is a composition and method for the prevention or treatment of diabetes. The composition and method of the invention promote beta-cell growth and inhibit apoptosis, induce immunological tolerance and block autoimmunity. The composition of the invention comprises a GABAergic (as islet beta-cell growth factor and autoimmune suppressor) and an incretin (as islet beta-cell growth factor and GABA facilitator). These are provided together in a single composition for the prevention or treatment of type I and type 2 diabetes in mammals, preferably for effective prevention or treatment of T1D.

In aspects, the GABAergic comprises a GABA molecule or its variant or derivates, or $GABA_AR$ agonist that effectively exerts beta-cell protection and suppresses islet beta-cell autoimmunity, such that the pancreatic islet cells are not destroyed. The incretine comprises at least one following peptide: GLP-1, DPP4 resistant form of GLP-1 or DPP-4 inhibitors, Ex4, GIP, their variant or derivates that effectively promotes islet beta-cell growth and stimulates endogenous GABA production and secretion, such that the pancreatic islet beta-cells are well protected and appropriately expended.

According to an aspect of an embodiment of the disclosure is composition to promote diabetogenic T-cell dependent immune inhibition, the composition comprising a GABAergic and a GLP-1/Ex4 peptide.

According to an aspect of an embodiment of the disclosure is composition to promote diabetogenic CD8+ T-cell dependent immune inhibition, the composition comprising a GABAergic and a GLP-1/Ex4 peptide.

According to another aspect of the invention is a composition comprising a GABAeric molecule that fused with an incretin molecule.

According to another aspect of the invention is a composition comprising a GABAeric molecule and a GLP-1 fusion protein or Ex4 fusion protein or a fusion protein of forementioned incretins.

In aspects of the invention the composition comprises nucleic acid sequences encoding a GABAeric molecule its variant or derivates, and a forementioned incretin peptide or a fusion protein of forementioned incretins.

According to an aspect of an embodiment of the disclosure is composition for the prevention or treatment of type I diabetes in a subject, said composition comprising a GABAergic selected from GABA, GABA synthesis enzyme GAD65, or GAD67, $GABA_AR$ agonist or variant or derivates thereof; and an GLP-1 or Ex4 or analogue or variant or fragment thereof.

In aspects of the invention the composition comprises nucleic acid sequences encoding a GABAeric molecule such as GABA, GABA synthesis enzyme GAD65 or GAD67, $GABA_AR$ agonist or variant or precursor of GABA such as glutamate or derivates thereof; and a forementioned incretin peptide GLP-1 or Ex4 or analogue or variant or fragment thereof or a fusion protein of forementioned incretins.

According to an aspect of an embodiment of the disclosure is a method of preventing or treating type I diabetes in a subject in need thereof, comprising administering to the subject an effective amount of a composition that increases beta-cell proliferation, reduces beta-cell apoptosis and suppresses beta-cell autoimmunity in a subject.

According to an aspect of an embodiment of the disclosure is a composition wherein the increased islet beta-cell proliferation/neogenesis and/or reduced apoptosis and suppressed beta-cell autoimmunity which provide increased beta-cell mass and function.

According to an aspect of an embodiment of the disclosure is the use of the composition of the invention for the preparation of a medicament for the prevention or treatment of type I diabetes in a subject.

Other features and advantages of an embodiment of the disclosure will become apparent from the following detailed description. It should be understood, however, that the detailed description and the specific examples while indicating embodiments of the invention are given by way of illustration only, since various changes and modifications within the spirit and scope of the invention will become apparent to those skilled in the art from said detailed description.

BRIEF DESCRIPTION OF THE DRAWINGS

An embodiment of the disclosure will be further understood from the following description with reference to the Figures, in which.

DETAILED DESCRIPTION

Figure 1:
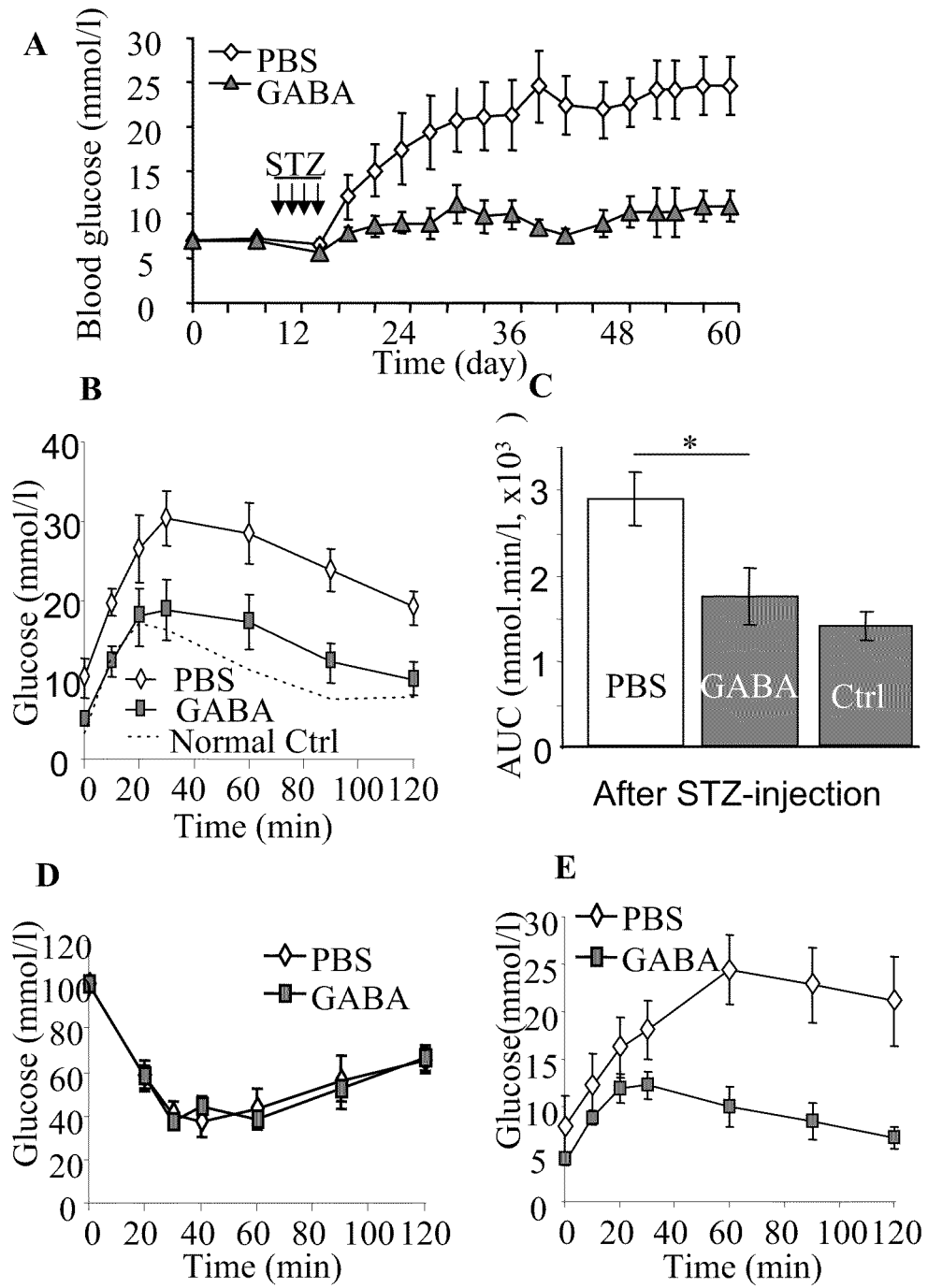
FIG. 1 A-I show treatment with GABA prevents development of diabetic hyperglycemia in MLDS-mice. Daily GABA injections maintained blood glucose at the relative lower levels in MLDS-mice, whereas untreated MLDS-mice developed severe diabetic hyperglycemia (A). The untreated MLDS mice developed impaired glucose tolerance, but the GABA-treated MLDS mice maintained close to normal glucose tolerance (dashed-line represents the glucose tolerance measured in the mice before the STZ-injections) (B). The area under curve shows that the glucose tolerance in the GABA-treated MLDS-mice was significantly improved (C). The insulin tolerance test shows that the both groups of MLDS-mice displayed similar insulin responsiveness (D) suggesting that GABA did not alter the insulin sensitivity in the MLDS-mice. The glucagon tolerance test shows that untreated MLDS-mice developed severe glucagon intolerance, which was largely improved in the MLDS-mice treated with GABA (E). The area under curve analysis shows that the improvement of glucagon intolerance by GABA was statistically significant (F). The GABA-treated MLDS-mice displayed significantly elevated circulating insulin levels compared to the untreated MLDS-mice (G) which was along with significantly reduced glucagon levels in these treated MLDS-mice (H). This provides a significantly increased insulin/glucagon ratio in the GABA-treated MLDS-mice (I).
Figure 1:
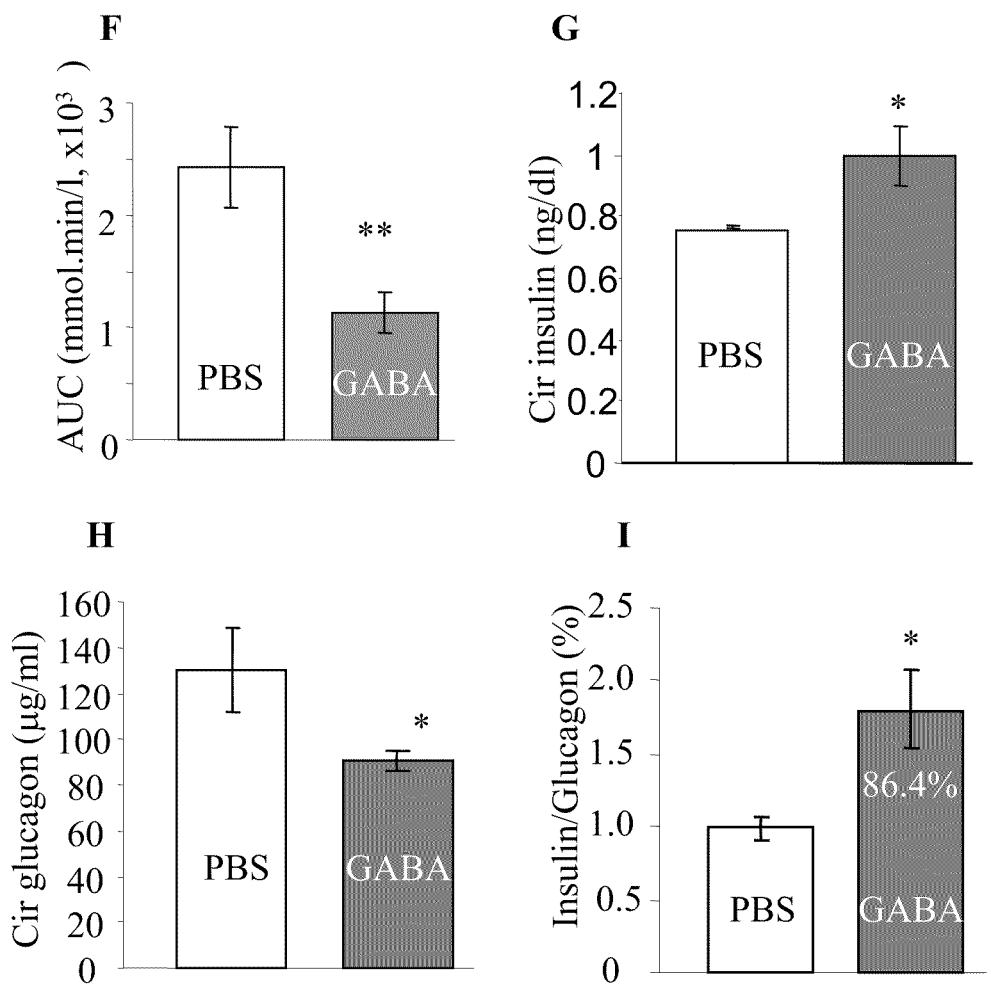

At the onset of type 1 diabetes (T1D), typically over 70-80% of beta-cells have been destroyed (Cnop M et al, 2005 Diabetes 54 Suppl 2:S97-107). This leads to the possibility that new beta-cells can be generated from the remaining beta-cells. Indeed, there has been a growing interest in the discovery of endogenous factors that stimulate beta-cell proliferation and regeneration. The incretin hormone GLP-1 appears to act this way, at least in rodents, although it has other anti-diabetic effects. Ex4, a mimic of GLP-1, has been clinically effective in T2D, but is only marginally effective in T1D-prone NOD mice (Hadjiyanni I et al, 2008 Endocrinology. 149, 1338-1349).

Because autoimmunity is persistent in type I diabetes subjects, control of autoimmunity with immunosuppression preferably specifically directed against the autoaggressive T cells is necessary for the replacement of islet cells and definitive treatment of this disease.

Disclosed herein is a new therapy for preventing and treating diabetes that consists of two powerful arms: islet beta-cell regeneration and simultaneously islet beta-cell autoimmunity suppression which are implemented by the combinatory effects of GABAergic and incretin, as exemplified by GABA and GLP-1.

Although it has been previously demonstrated that GABA could reduce T1D induction by streptozotocin in rats (Nakagawa T, et al, J Nutr Sci Vitaminol (Tokyo). 2005 August; 51(4):278-82), the therapeutic effects of GABA in a subject that has already developed diabetes or diabetic hyperglycemia are disclosed herein.

It is demonstrated herein that GABA remarkably prevented development of hyperglycemia in multiple-low-dose streptozotocin-induced diabetes mice (MLDS). Treatment with GABA also completely reversed diabetic hyperglycemia in established T1 in MLDS mice. The in vitro studies provided new and important evidence that the therapeutic effects of GABA on T1D in MLDS mice were through promotion of islet beta-cell growth, enhancing beta-cell mass and inhibition of autoimmune and/or inflammatory injury to the beta-cells.

The data disclosed herein also show that GABA prevented diabetic hyperglycemia in autoimmune NOD mice. This was associated with reduced immune-cell infiltration in the islets, increased beta-cell mass and elevated circulating insulin levels in the NOD mice.

While GABA has significant effects in preventing onset of diabetes in both MLDS, and NOD mice, as a demonstration herein, GABA completely reversed diabetes after induction of diabetes by drug in MLDS mice. Although the beneficial effects were transient in autoimmune NOD mice treated with GABA after the onset of diabetes. It is conceivable that such transient reversing effects may be significantly beneficial to subject of T1D in human.

Further, as also disclosed herein the combination therapy of GABA with incretin such as for example, GLP-1/Ex4, resulted in non-transient reversing effects. As shown, co-administration of GABA and GLP-1 achieved remission in established T1D in NOD mice.

Accordingly, disclosed herein is an effective therapy using a GABAergic compound, for example GABA, and an effective combination therapy using a GABAergic compound and an incretin, for example GLP-1, for the treatment of type 1 diabetes. The prior art references do not specifically describe or suggest combining an incretin with a GABAergic, and effects of such combination.

Important biological effects of the GABAergic, in particular suppression of inflammation, promotion of islet beta-cell growth and inhibiting islet beta-cell autoimmunity are demonstrated. Without wishing to be bound to theory, the treatment of type 1 diabetes may require both restoration of islet beta-cell mass and suppression of the autoimmune process. No current therapy achieves both goals efficiently. The incretin hormone GLP-1 and Exendin-4 (Ex4), a mimic of GLP-1, has beta-cell regenerative effects and has thus been clinically effective in T2D, but is only marginally effective in T1D-prone diabetes subjects (Hadjiyanni I et al, 2008 Endocrinology. 149, 1338-1349). The combined therapy of GABAergic and incretin(s), exemplified by the combination of GABA and GLP-1 and/or Ex4 exerts synergistic effect—the effects are more than additive. For example, the combined therapy of GABA and GLP-1 and/or exendin-4 completely reverses diabetic hyperglycemia, presumably through beta-cell regeneration and suppression of the autoimmune process.

Accordingly, an aspect of the disclosure includes a method of treating type 1 diabetes (T1D), said method comprising administering to a subject having T1D a therapeutically effective amount of a composition comprising a GABAergic compound, or a pharmaceutically acceptable salt thereof.

The term "GABAergic compound" as used herein means a compound that transmits or secretes gamma-aminobutyric acid and includes GABA, glutamate, GABA-synthesizing enzyme GAD65, GAD67, GABA receptor agonist, in particular type A GABA receptor ($GABA_AR$) agonists and/or derivates thereof a recombinant and/or a synthesized version or a pharmaceutically acceptable salt, solvate or prodrug thereof as well as mixtures thereof. For example, GABA receptor antagonists include bicuculline, metrazol, benzodiazepine, flumazenil or propofol and $GABA_AR$ agonists include muscimol, phenobarbital, THIP, or isoguvacine.

The term "GABA" as used herein means a compound having the formula:

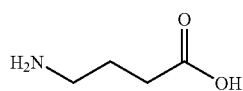

or a pharmaceutically acceptable salt, solvate or prodrug thereof as well as mixtures thereof.

In an embodiment, the GABAergic compound is selected from GABA, GAD65, GAD67, a GABA receptor agonist, a type A GABA receptor ($GABA_AR$) agonist, or GABA variants selected from a GABA chemical conjugant, GABA fusion or GABA with a chemically modified or replaced amino group, or derivates thereof.

In an embodiment, wherein said GABA fusion is selected from GABA-albumin fusion or GABA-IgGFc fusion; or wherein said GABA with a chemically modified or replaced amino group is selected from said amino group modified or replaced with a halogen group, an alkyl group, a cycloalkyl group, a methyl group, an alkoxy group, an aryl group, or a heteroaryl group.

In an embodiment the composition administered further comprises an effective amount of an incretin. In an embodiment, the incretin is selected from glucagon-like peptide-1 (GLP-1), exendin-4 (Ex4) or variants or derivates thereof.

The term "incretin" as used herein means a type of gastrointestinal hormone that causes an increase in the amount of insulin released from the beta cells of the islets of Langerhans after eating and that inhibits glucagon release from the alpha cells of the Islets of Langerhans, and includes a recombinant and/or a synthesized version or a pharmaceutically acceptable salt, solvate or prodrug thereof as well as mixtures thereof. Examples include glucagon-like peptide-1 (GLP-1), and Gastric inhibitory peptide (also known as glucose-dependent Insulinotropic peptide or GIP. Both GLP-1 (active fragment GLP-1 (7-36)) and GIP are rapidly inactivated by the enzyme dipeptidyl peptidase 4 (DPP-4). Several long-lasting analogs of GLP-1 that have insulinotropic activity have been developed, including Exendin-4 (Ex4), also known as exenatide, and Exendin-9 (Ex9) and one, exenatide, has been approved for use in the U.S.

The term "incretin activity" includes for example compounds that have similar effect to incretin, for example DPP-IV inhibitors which prevent GLP-1 from being inactivated. For example, sitagliptin, vildagliptin, alogliptin, and saxagliptin are known DPP-IV inhibitors which are proposed for treatment of type 2 diabetes.

The term "GLP-1" as used herein means any GLP-1 polypeptide or nucleic acid from any species, preferably human, naturally occurring or variants retaining GLP-1 activity including GLP-1 active fragments (e.g. GLP-1(7-36), GLP-1 active fusions (as described in US 20090181912 and US 20090016968 which are each specifically incorporated herein by reference), and DPP-IV resistant variants such as GLP-1A8X, where X is any amino acid except A. Also included are a recombinant and/or a synthesized version or a pharmaceutically acceptable salt, solvate or prodrug thereof as well as mixtures thereof. In an embodiment, X is G. In another embodiment, GLP-1 is selected from GLP-1(7-37) OH, GLP-1(7-36)amide-1, a DPPIV resistant GLP-1, a GLP-1 fusion protein, and fragments and derivatives thereof. In another embodiment, the GLP-1 comprises an amino acid sequence or nucleic acid sequence encoding such amino acid sequence described herein.

The term "Exendin-4" as used herein means any Exedin-4 polypeptide or nucleic acid from any species, preferably human, naturally occurring or variant retaining Exendin-4 activity including Ex4 active fragments, Ex4 active fusions (as described in US 20090181912 and US 20090016968 which are each specifically incorporated herein by reference). Also included are a recombinant and/or a synthesized version or a pharmaceutically acceptable salt, solvate or prodrug thereof as well as mixtures thereof.

In an embodiment, the GLP-1 or variant thereof is selected from GLP-1(7-37)OH, GLP-1(7-36)amide-1, a DPPIV resistant GLP-1, a GLP-1 fusion protein, and fragments and derivatives thereof.

Another aspect includes a composition, comprising a GABAergic compound and an incretin and optionally a pharmaceutically suitable carrier. In an embodiment, the GABAergic compound is a compound described herein. In another embodiment, the incretin is an incretin described herein.

In an embodiment, the incretin is GLP-1. In another embodiment, the incretin is Ex4. The incretin can be comprised in a composition or administered as a polypeptide comprising an amino acid sequence described herein, a variant of a polypeptide or a nucleic acid encoding a polypeptide or variant described herein.

GLP-1 or Ex4 is a polypeptide variant, wherein said GLP-1 polypeptide variant comprises about 70% to about 99.9% sequence identity with GLP-1 of SEQ ID NO.1; or wherein said Ex4 polypeptide variant comprises a polypeptide from about 70% to about 99.9% sequence identity with Ex4 of SEQ ID NO.2.

In an embodiment, the composition comprises, or the method involves administering, one or more polypeptides selected from SEQ ID NO:1-7, or comprising one or more nucleic acids encoding said polypeptides selected from SEQ ID NO:1-7.

In another embodiment, the DPPIV resistant GLP-1 is GLP-1A8X, wherein X is any amino acid other than A, optionally. In another embodiment, the DPPIV resistant GLP-1 is a GLP-1 mimetic, for example with modification including N-acetyl-GLP-1 in which the N-terminal of GLP-1 is modified by glycation (as described by Liu H K et al, Cell Biology International 2004, 28(1):69-73). Other DPPIV resistant GLP-1 mimetics are GLP-1 analogues with alterations in the N-terminal position 1 including N-methylated- (N-me-GLP-1), α-methylated (α-me-GLP-1), desamidated- (desamino-GLP-1) and imidazole-lactic-acid substituted GLP-1 (imi-GLP-1) (as described by Gallwitz B et al, Regulatory Peptides 2000, 86, 103-111). In another embodiment, the GLP-1 comprises a N-terminal extension of GLP-1 by a single amino acid such as H, A or G (as described by Oh J Y et al Bull. Korean Chem. Soc. 2009, 30(10):2471-2474). The N-terminal modification of GLP-1 such as by covalently linking GLP-1 to a fatty acid chain (as described by Juhl C B et al, Diabetes. 2002 51(2):424-9). In a further embodiment, the GLP-1 fusion protein comprises an IgG Fc or albumin.

In yet another embodiment, the GABAergic and incretin are separate molecules, comprised for example in a mixture or are fused together to form a single GABAergic/incretin fusion polypeptide or nucleic acid encoding said polypeptide or variants or derivatives thereof. The said fusion polypeptide or nucleic acid can be made using protein recombinant method which is obvious to a person of skill in the art.

The term "mixture" as used herein, means a composition comprising two or more of compounds. In an embodiment a mixture is a mixture of two or more distinct compounds. In a further embodiment, when a compound is referred to as a "mixture", this means that it can comprise two or more "forms" of the compounds, such as, salts, solvates, prodrugs or, where applicable, stereoisomers of the compound in any ratio. A person of skill in the art would understand that a compound in a mixture can also exist as a mixture of forms. For example, a compound may exist as a hydrate of a salt or as a hydrate of a salt of a prodrug of the compound. All forms of the compounds disclosed herein, in and ratio or combination, are within the scope of the present disclosure.

The term "synergistic" as used herein means the enhanced or magnified effect of a combination on at least one property compared to the additive individual effects of each component of the combination. Synergism can be assessed and quantified for example by analyzing the Data by the Calcusyn median effect model where the combination index (CI) indicates synergism (CI<0.9), additively (CI=0.9-1.1) or antagonism (CI>1.1). CIs of <0.3, 0.3-0.7, 0.7-0.85, 0.85-0.90, 0.90-1.10 or >1.10 indicate strong synergism, synergism, moderate synergism, slight synergism, additive effect or antagonism, respectively. The CI is the statistical measure of synergy.

The term "prodrug" as used herein refers to a derivative of an active form of a known compound or composition which derivative, when administered to a subject, is gradually converted to the active form to produce a better therapeutic response and/or a reduced toxicity level. In general, prodrugs will be functional derivatives of the compounds disclosed herein which are readily convertible in vivo into the compound from which it is notionally derived. Prodrugs include, without limitation, acyl esters, carbonates, phosphates, and urethanes. These groups are exemplary, and not exhaustive, and one skilled in the art could prepare other known varieties of prodrugs. Prodrugs may be, for example, formed with available hydroxy, thiol, amino or carboxyl groups. For example, the available OH and/or $NH_2$ in the compounds of the disclosure may be acylated using an activated acid in the presence of a base, and optionally, in inert solvent (e.g. an acid chloride in pyridine). Some common esters which have been utilized as prodrugs are phenyl esters, aliphatic ($C_8$-$C_{24}$) esters, acyloxymethyl esters, carbamates and amino acid esters. In certain instances, the prodrugs of the compounds of the disclosure are those in which the hydroxy and/or amino groups in the compounds is masked as groups which can be converted to hydroxy and/or amino groups in vivo. Conventional procedures for the selection and preparation of suitable prodrugs are described, for example, in "Design of Prodrugs" ed. H. Bundgaard, Elsevier, 1985.

The term "solvate" as used herein means a compound or its pharmaceutically acceptable salt, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions.

Where the compounds according to the disclosure possess more than one or more asymmetric centre, they may exist as "stereoisomers", such as enantiomers and diastereomers. It is to be understood that all such stereisomers and mixtures thereof in any proportion are encompassed within the scope of the present disclosure. It is to be understood that while the stereochemistry of the compounds of the disclosure may be as provided for in any given compound shown herein, such compounds may also contain certain amounts (e.g. less than 20%, less than 10%, less than 5%) of compounds having alternate stereochemistry.

The term "subject" as used herein includes all members of the animal kingdom including mammals, and suitably refers to humans.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "Treatment" can also mean prolonging survival as compared to expected survival if not receiving treatment. "Treating" and "treatment" as used herein also include prophylactic treatment. For example, a subject with early stage myeloma can be treated to prevent progression or alternatively a subject in remission can be treated with a compound or composition described herein to prevent recurrence. Treatment methods comprise administering to a subject a therapeutically effective amount of a compound described herein and optionally consists of a single administration, or alternatively comprises a series of applications. For example, the compounds described herein may be administered at least once a week. However, in another embodiment, the compounds may be administered to the subject from about one time per week to about once daily for a given treatment. In another embodiment, the compound is administered twice daily. The length of the treatment period depends on a variety of factors, such as the severity of the disease, the age of the patient, the concentration, the activity of the compounds described herein, and/or a combination thereof. It will also be appreciated that the effective dosage of the compound used for the treatment or prophylaxis may increase or decrease over the course of a particular treatment or prophylaxis regime. Changes in dosage may result and become apparent by standard diagnostic assays known in the art. In some instances, chronic administration may be required. For example, the compounds are administered to the subject in an amount and for a duration sufficient to treat the patient.

Prevention as used herein is any procedure which reduces the burden of mortality or morbidity from disease. To certain extent, prevention may avoid the development of a disease. Furthermore, a procedure of prevention usually starts before the obvious sickness of the disease. In autoimmune disease such as T1D which is due to autoimmune destruction of the islet beta-cells and subsequent insulin deficiency and hyperglycemia, an effective approach that blocks the autoimmunity may be effective in preventing the development of T1D. In a contrary, treatment is a procedure that treats a disease that may lead to its cure. In most cases, treatments more often ameliorate a disease only for as long as the treatment is continued. At the onset of T1D over 70-80% of islet beta-cells have been destroyed (Cnop M et al, 2005 Diabetes 54 Suppl 2:S97-107). It appears that an approach that only suppresses islet autoimmunity is not sufficient to ameliorate the disease. A strategy involving islet beta-cell regeneration appears to be required to replace the injured islet beta-cells, in addition to the specific immune suppression.

The disclosure provides a demonstration of prevention of development of diabetes in different mouse models however the emphasis was on the treatment—reversing disease in a subject with T1D, using various T1D mouse models. It is conceivable that an effective treatment approach may be effective to prevent the disease. In contrast, an effective preventive approach may not be necessary useful to achieve therapeutic effects.

The disclosure also includes in an embodiment a method of preventing development of diabetic hyperglycemia comprising administering a GABAergic compound and an incretin.

Another embodiment provides a method of improving/preventing glucagon intolerance comprising administering a GABAergic compound and an incretin.

A further embodiment provides a method of increasing insulin glucose ratio comprising administering a GABAergic compound and an incretin.

In an embodiment, the GABAergic compound and incretin are administered daily. A further embodiment includes a method of improving glucose tolerance comprising administering a GABAergic compound and an incretin.

Yet a further embodiment includes a method of reducing blood sugar levels comprising administering a GABAergic compound and an incretin.

Another embodiment includes a method of reducing diabetic symptoms comprising administering a GABAergic compound and an incretin. In an embodiment, the diabetic symptoms include for example polydipsia and polyuria.

In an embodiment, the composition is administered by a method selected from topical administration, oral administration, aerosol administration, intraperitoneal injection, intravenous injection and/or intramuscular injection. In another embodiment, the GLP-1 or Ex4 is a polypeptide variant, wherein said GLP-1 polypeptide variant comprises about 70% to about 100% sequence identity with GLP-1 of SEQ ID NO.1; or wherein said Ex4 polypeptide variant comprises a polypeptide from about 70% to about 100% sequence identity with Ex4 of SEQ ID NO.2. In yet another embodiment, the composition administered comprises one or more polypeptides selected from SEQ ID NO:1-7, or comprising one or more nucleic acids encoding said polypeptides selected from SEQ ID NO:1-7. In an embodiment, one or more of the GABAergic compound or incretin in said composition is provided as a nucleic acid sequence, optionally comprised in a vector, wherein the vector is optionally a non-viral vector, a viral delivery vehicle, or for bacterial or mammalian expression.

In a further embodiment, the dosage of the composition is 0.01-10 mmol/kg of GABAergic compound and 0.02 to 1000 nmol/kg of incretin or between about 0.002-2 mg/kg of GABAergic compound and 0.2-1000 nmol/kg of incretin; wherein the GABAergic compound and incretin are preferably GABA and GLP-1 and/or Ex4 polypeptides.

In another embodiment, the composition comprises nucleic acid DNA encoding the respective compound in composition for use may be about 1 µg/kg of body weight to 10 µg/kg of body or between 0.1 to 100 µg/kg of body weight. Suitable concentrations of the DNA vaccine for use comprise 0.1 to about 1000 microgram of DNA.

The term "pharmaceutically acceptable salt" means an acid addition salt or a basic addition salt which is suitable for or compatible with the treatment of patients. The formation of a desired compound salt is achieved using standard techniques. For example, the neutral compound is treated with an acid or base in a suitable solvent and the formed salt is isolated by filtration, extraction or any other suitable method.

As used herein, "contemporaneous administration" and "administered contemporaneously" means that the GABAergic and incretin are administered to a subject such that they are each biologically active in the subject at the same time. The exact details of the administration will depend on the pharmacokinetics of the substances in the presence of each other, and can include administering one substance within 24 hours of administration of another, if the pharmacokinetics are suitable. Designs of suitable dosing regimens are routine for one skilled in the art. In particular embodiments, two substances will be administered substantially simultaneously, i.e. within minutes of each other, or in a single composition that comprises both substances.

The term "combination therapy" or "in combination with" as used herein means two or more substances, for example GABA and GLP-1 or GABA and Ex4, are administered to a subject over a period of time, contemporaneously or sequentially e.g. the substances are administered at the same time or at different times within the period of time in a regimen that will provide beneficial effects of the drug combination, at similar or different intervals. For example, the combination therapy is intended to embrace co-administration, in a substantially simultaneous manner such as in a single dosage form e.g. a capsule, having a fixed ratio of active ingredients or in multiple, separate dosage forms, e.g. capsules, for each substance. The compounds may or may not be biologically active in the subject at the same time. As an example, a first substance is administered weekly, and a second substance administered daily. The exact details of the administration will depend on the pharmacokinetics of the two substances. Designs of suitable dosing regimens are routine for one skilled in the art.

As used herein, the phrase "dosage form" refers to the physical form of a dose for example comprising a GABAergic and/or an incretin, and includes without limitation tablets, including enteric coated tablets, caplets, gelcaps, capsules, ingestible tablets, buccal tablets, troches, elixirs, suspensions, syrups, wafers, liposomal formulations and the like. The dosage form may be solid or liquid. Liposomal formulations, can for example be used to administer multiple compounds at fixed ratios.

As used herein, the phrase "effective amount" or "therapeutically effective amount" means an amount effective, at dosages and for periods of time necessary to achieve the desired result. For example in the context or treating a diabetes such as a T1D, an effective amount is an amount that for example induces remission, promotes islet beta-cell regeneration, suppress beta-cell apoptosis, controls islet autoimmunity and/or reduces hyperglycemia compared to the response obtained without administration of the compound. Effective amounts may vary according to factors such as the disease state, age, sex and weight of the animal. The amount of a given compound that will correspond to such an amount will vary depending upon various factors, such as the given drug or compound, the pharmaceutical formulation, the route of administration, the type of disease or disorder, the identity of the subject or host being treated, and the like, but can nevertheless be routinely determined by one skilled in the art.

The compositions described herein can be prepared by per se known methods for the preparation of pharmaceutically acceptable compositions that can be administered to subjects, such that an effective quantity of the active substance is combined in a mixture with a pharmaceutically acceptable vehicle.

In an embodiment, the composition is a pharmaceutical composition.

Suitable vehicles are described, for example, in Remington's Pharmaceutical Sciences (2003—20$^{th}$ Edition). On this basis, the compositions include, albeit not exclusively, solutions of the substances in association with one or more pharmaceutically acceptable vehicles or diluents, and contained in buffered solutions with a suitable pH and iso-osmotic with the physiological fluids.

Pharmaceutical compositions include, without limitation, lyophilized powders or aqueous or non-aqueous sterile injectable solutions or suspensions, which optionally further contain antioxidants, buffers, bacteriostats and solutes that render the compositions substantially compatible with the tissues or the blood of an intended recipient. Other components that are optionally present in such compositions include, for example, water, surfactants (such as Tween™), alcohols, polyols, glycerin and vegetable oils. Extemporaneous injection solutions and suspensions may be prepared from sterile powders, granules, tablets, or concentrated solutions or suspensions. The composition can be supplied, for example but not by way of limitation, as a lyophilized powder which is reconstituted with sterile water or saline prior to administration to the subject.

Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1(2,3-dioleyloxy)propyl)N,N,N-trimethylammonium chloride (DOTMA), diolesylphosphotidyl-ethanolamine (DOPE), and liposomes. Such compositions should contain a therapeutically effective amount of the compound(s), together with a suitable amount of carrier so as to provide the form for direct administration to the subject.

In an embodiment, the compositions described herein are administered for example, by parenteral, intravenous, subcutaneous, intramuscular, intracranial, intraorbital, ophthalmic, intraventricular, intracapsular, intraspinal, intracisternal, intraperitoneal, intranasal, aerosol or oral administration.

Compositions for nasal administration can conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Wherein the route of administration is oral, the dosage form may be for example, incorporated with excipient and used in the form of enteric coated tablets, caplets, gelcaps, capsules, ingestible tablets, buccal tablets, troches, elixirs, suspensions, syrups, wafers, and the like. The oral dosage form may be solid or liquid.

In an embodiment, the disclosure describes a pharmaceutical composition wherein the dosage form is a solid dosage form. A solid dosage form refers to individually coated tablets, capsules, granules or other non-liquid dosage forms suitable for oral administration. It is to be understood that the solid dosage form includes, but is not limited to, modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., as of molecular sieving type particles, or, a fine hollow permeable fiber bundle, or chopped hollow permeable fibers, agglomerated or held in a fibrous packet. Timed-release compositions can be formulated, e.g. liposomes or those wherein the active compound is protected with differentially degradable coatings, such as by microencapsulation, multiple coatings, etc. It is also possible to freeze-dry the compounds described herein and use the lyophilizates obtained, for example, for the preparation of products for injection.

Compositions suitable for buccal or sublingual administration include tablets, lozenges, and pastilles, wherein the active ingredient is formulated with a carrier such as sugar, acacia, tragacanth, and/or gelatin and/or glycerin.

In another embodiment, the disclosure describes a pharmaceutical composition wherein the dosage form is a liquid oral dosage form. A person skilled in the art would know how to prepare suitable formulations. Conventional procedures and ingredients for the selection and preparation of suitable formulations are described, for example, in Remington's Pharmaceutical Sciences (2003—20th edition) and in The United States Pharmacopeia: The National Formulary (USP 24 NF19) published in 1999.

In another embodiment, the disclosure describes a pharmaceutical composition wherein the dosage form is an injectable dosage form. An injectable dosage form is to be understood to refer to liquid dosage forms suitable for, but not limited to, intravenous, subcutaneous, intramuscular, or intraperitoneal administration. Solutions of compounds described herein can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. Conventional procedures and ingredients for the selection and preparation of suitable formulations are described, for example, in Remington's Pharmaceutical Sciences (2003—20th edition) and in The United States Pharmacopeia: The National Formulary (USP 24 NF19) published in 1999.

The pharmaceutical forms suitable for injectable use include sterile aqueous solutions or dispersion and sterile powders for the extemporaneous preparation of sterile injectable solutions or dispersions. In all cases the form must be sterile and must be fluid to the extent that easy syringability exists.

The feasibility of the present therapy of combined GABAeric and incretin is supported by in vivo and in vitro data. Therefore, in an embodiment, the disclosure provides a specific composition and method of preventing and/or treating type I diabetes in a subject. In an embodiment, the composition is administered to a subject in need thereof and for example increases beta-cell proliferation, reduces beta-cell apoptosis and/or controls immunity specifically that leads to enhancement of beta-cell mass, the beta-cell function and insulin secretion. The composition comprises in an embodiment, a GABAergic and an incretin. In another embodiment, the GABAergic comprises a GABA compound or its variant or derivates or GABA precursor like glutamate, or $GABA_AR$ agonist that effectively exerts beta-cell protection and decreases autoimmunity, such that the pancreatic islet cells are not destroyed. The synergic effects of GABA and GLP-1/Ex4 for example, appears to result in a reciprocity outcome such as modulation of endogenous GABA and GLP-1 production/secretion, such that the pancreatic islet beta-cells are well protected and appropriately expended in a subject with T1D. In an aspect, the disclosure includes a method of treating type 1 diabetes (T1D), said method comprising administering to a subject having T1D a therapeutically effective amount of a composition comprising a GABAergic, or a pharmaceutically acceptable salt thereof; wherein said administering does effectively promote islet beta-cell regeneration, suppress beta-cell apoptosis and/or control islet autoimmunity.

In an embodiment, the composition further comprises an incretin or a compound with incretin activity. In an embodiment, the compound with incretin activity is a DPP-4 inhibitor.

In one embodiment, the composition is made to contain GABA and GLP-1. Various components thereof can be made to contain GABA amino acid/GLP-1 peptides or GABA-synthesing enzyme GAD65/67 and GLP-1 or its analogues such as Ex4 and DPP-4 inhibitors.

In an embodiment, GABAergic is selected from GABA, GAD65, GAD67, or a GABA receptor agonist.

In an embodiment, GABAergic is GABA. GABA is an amino acid which is commercially available and it can be synthesized using a traditional standard method. Wherein said incretin is selected from glucagon-like peptide-1 (GLP-1), exendin-4 (Ex4) polypeptides or variants or derivates thereof. Ex4 (Byetta) is presently commercially available for the treatment of type 2 diabetes.

In an embodiment, GABA is selected from naturally existent form or variants or derivates thereof. The variants or derivates including but not limited to a form of protein fusion, or chemical conjugant, or of chemical modification or replacement of amino group of GABA thereof.

In an embodiment, GABA is selected in chemical modification. or pharmaceutically acceptable substance; wherein said N-terminal modification or replacement is achieved through a replacement by a chemical group. In an embodiment, the chemical group includes but is not limited to a halogen group, or a alkyl group, or a cycloalkyl group, or a methyl group, or an alkoxy group, or an aryl group, or a heteroaryl group, or a chaneical group thereof.

In one embodiment, the incretin comprises at least one of the following peptides or nucleic acid encoding such peptide: GLP-1, DPP4 resistant form of GLP-1 (or DPP-4 inhibitors), Ex4, GIP, their variant or derivates that effectively prevents beta-cell death and promotes islet beta-cell proliferation and neogenesis.

In an embodiment, the GLP-1 polypeptide is selected from the group consisting of GLP-1(7-37)OH, GLP-1(7-36) amide-1, a DPPIV resistant GLP-1 and fragments and variants thereof. In an embodiment, the DPPIV resistant GLP-1 is GLP-1A8G. In an embodiment, the polypeptides and/or nucleic acids are selected from naturally existent form or a form of fusion protein or encoding such, or chemical conjugant, or of chemical modification or replacement of the amino group thereof.

The fusion in an embodiment includes fusion to albumin or an IgG Fc portion. In an embodiment, the albumin molecule is selected from human albumin; and/or the IgG is selected from human IgG and said human IgG is IgG1, IgG2, IgG3, IgG4, preferably IgG2 and IgG4.

In an embodiment, the GABAergic compound and ithe ncretin are selected from separated individual, or are selected from a form that GABAergic and GLP-1/Ex4 are fused together to form a single GABAergic fusion polypeptides or variants or derivates thereof.

In an embodiment, the GLP-1 polypeptide variant comprises a polypeptide from about 70% to about 95% sequence identity with GLP-1 of SEQ ID NO.1; or wherein said Ex4 polypeptide variant comprises a polypeptide from about 70% to about 95% sequence identity with Ex4 of SEQ ID NO.2.

In an embodiment, the composition comprises a pharmaceutically acceptable carrier.

In an embodiment, the composition is for the treatment of type I diabetes.

In an embodiment, the composition is administered by a method selected from the group consisting of topical administration, oral administration, aerosol administration, intraperitoneal injection, intravenous injection and/or intramuscular injection.

In another embodiment, the composition is administered by a method selected from the group consisting intramuscular injection of nucleic acid sequences encoding composition of claim 17; wherein the vector is optionally a non-viral vector, a viral delivery vehicle, or for bacterial or mammalian expression.

A further aspect includes a host cell expressing a GABAergic and an incretin.

In an embodiment, the dosage of the composition is 0.01-10 mmol/kg of GABAergic and 0.02 to 1000 nmol/kg of incretin (i.e. GABA:GLP-1/Ex4) or between about 0.002-2 mg/kg of GABAergic and 0.2-1000 nmol/kg of incretin; wherein the GABAergic and incretin are preferably GABA and GLP-1/Ex4.

In another embodiment, the composition is delivered by gene therapy, DNA encoding the respective compound in composition for use may be about 1 µg/kg of body weight to 10 µg/kg of body or between 0.1 to 100 µg/kg of body weight. Suitable concentrations of the DNA vaccine for use comprise 0.1 to about 1000 microgram of DNA.

In one embodiment, the therapeutic composition that contains GABAergic compound and GLP-1 or GLP-1 like incretins aforementioned can effectively enlarge the islet beta-cell mass and enhance beta-cell functions and simultaneously promote diabetogenic T-cell dependent immune inhibition and such that effectively prevent or reserve the loss of islet beta-cell during the development of T1D of islet beta-cell during the development of T1D.

In one embodiment, the therapeutic composition suppresses diabetogenic T-cell dependent immune destruction in the islet beta-cells. The said diabetogenic T-cells are CD8+ T-cells. It is known that the persistent T-cell dependent assault specifically to the islet beta-cells that causes beta-cells loss and consequent diabetic hyperglycemia in a subject with T1D.

The GABAergic effects are mainly executed through activation of the GABA receptors. In pancreatic islets, while GABA is specifically produced in the beta-cells the GABA receptors are expressed in both the beta-cells and alpha-cells. It is important that GABA receptor expressed in the T-lymphocytes (U.S. Pat. No. 6,350,769) provides explanation underlies that GABA can suppress T-cell autoimmunity. GLP-1 receptor mainly expressed in the islet beta-cells and to certain degree in the gut and brain (Brubaker P L, Drucker D J 2004 Endocrinology 145:2653-2659). Although there no previous report showing that GLP-1 receptors is expressed in the T-cells, it is possible the GLP-1 may have potential effect on the T-lymphocytes indirectly through modulation of GABA produced and secreted from islet beta-cells or other peripheral tissues in response to GLP-1 action.

In one embodiment, one or more of the components of the composition all are provided within suitable vectors as nucleic acid sequences, operably linked to a promoter. Administration of such relevant nucleotide sequence may be provided in the composition as a DNA vector. The DNA vector comprises at least one plasmid having a nucleotide sequence which is expressed by the cellular machinery of the subject to be injected. The nucleotide sequence of the plasmid encodes one or more peptides capable of induction of GABAergic and GLP-1 actions to enhance the islet beta-cell function and to tolerance and decreasing autoimmune recognition. In an embodiment, the plasmids encode GABAergic compound and incretin and optionally GABA, GAD65 or GAD67 and an GLP-1 or Ex4. In aspects of an embodiment of the disclosure, the GABAergic compounds are selected from one or more of GABA, GAD65, GAD67, GABA receptor agonist. The fusion forms of GABAergic molecules i.e. a GABA molecule fused with an albumin molecule or other chemical conjugate and thereof to exert GABAergic effects are also feasible. Accordingly, the plasmids in an embodiment, encode incretin molecule that comprises at least one following peptide: GLP-1, GLP-1(7-37)OH or GLP-1(7-36) amide as well as the DPP4 resistant form of GLP-1 (or DPP-4 inhibitors), Ex4, GIP, their variant or derivates that effectively promotes islet beta-cell growth and stimulates endogenous GABA production and secretion to promote the pancreatic islet cell functions. In another embodiment, the incretin peptide of the composition can comprise active GLP-1 molecules and IgG heavy chain constant regions (GLP-1/IgG-Fc). The construction of fusion proteins combining GLP-1 with an IgG-Fc molecule forms a new molecule that possess enhanced GLP-1 actions and advantages of the IgG-Fc molecule i.e. increased ligand avidity and immunological tolerance. The GLP-1 peptide in aspects is native or is DPP-IV (Dipeptidyl Peptidase IV) resistant. The IgG may be mouse or human. In aspects, a mouse IgG may be $IgG_1$. A human IgG may be selected from $IgG_1$, $IgG_2$, $IgG_3$ and $IgG_4$. Or IgGE or IgGM. The GLP-1 polypeptide may be human or mouse sequence as they are identical. The GLP-1 polypeptide may be a variant or fragment of the native sequence. The GLP-1 polypeptide may be GLP-1(7-37)OH or GLP-1(7-36)amide.

Rationally, such GLP-1/Ex4 fusions can be made with a human albumin or other chemical conjugants to prolong the lifetime of GLP-1/ex4 or its variants and derivates in the circulation and to enhance the GLP-1 actions.

A further aspect of the disclosure includes the use of all the aforementioned compounds for prevention and treatment of diabetes, such as type I diabetes patients. A further aspect includes use of all the aforementioned compounds for preparation of a medicament for prevention and treatment of diabetes, such as type I diabetes. Yet a further aspect includes a pharmaceutical composition, such as a prophylactic composition, for all the aforementioned uses. Changes which result in production of a chemically equivalent or chemically similar amino acid sequence are included within the scope of an embodiment of the disclosure. The composition of combined therapy sharing structure and sequence identity to GABA or /GLP-1 Ex4 are within the scope of an embodiment of the disclosure and may be readily tested to ensure that they are suitable for use in the methods of the invention. U.S. Pat. No. 6,268,343 (incorporated by reference in its entirety), describes a number of GLP-1 derivatives and variants. Variants of the polypeptides of an embodiment of the disclosure may occur naturally, for example, by mutation, or may be made, for example, with polypeptide engineering techniques such as site directed mutagenesis, which are well known in the art for substitution of amino acids. For example, a hydrophobic residue, such as glycine can be substituted for another hydrophobic residue such as alanine. An alanine residue may be substituted with a more hydrophobic residue such as leucine, valine or isoleucine. A negatively charged amino acid such as aspartic acid may be substituted for glutamic acid. A positively charged amino acid such as lysine may be substituted for another positively charged amino acid such as arginine. GABA is an amino acid with molecular formula of $C_4H_9NO_2$ and molecular weight of 103.12 g/mol. Variants of GABA structure are contemplated to be within the scope of the present disclosure, for example variants may occur naturally, or for example, by chemical modifications or other relevant methods which are well known in the art for modification of amino acids. For example, the amino-group can be replaced by other chemical group or structure, such as Fmoc-group to form Fmoc-GABA. Or, GABA is acetylated at the N-terminus to form acetylated GABA. Those with skill in the art recognize that a variety of techniques are available for such replacement or modifications with the same or similar desired compound activity as the corresponding compound of an embodiment of the disclosure but with more favorable activity than the compound with respect to solubility, stability, and/or susceptibility to hydrolysis and proteolysis. See, for example, A. Abell, ADVANCES IN AMINO ACID MIMETICS AND PEPTIDOMIMETICS, VOLUME 1, 1. Examples of amino acid mimetics are described in U.S. Pat. Nos. 5,733,868, 3,642,858, 7,157,264. Other patents describing how to make and use amino acid mimetics include, for example in, U.S. Pat. No. 7,384,979, WO/2003/031472 WO9407912, WO/2005/047503 are incorporated herein by reference in their entirety. Furthermore, those with skill in the art recognize that a variety of techniques are available for constructing polypeptide mimetics with the same or similar desired compound activity as the corresponding polypeptide compound of an embodiment of the disclosure but with more favorable activity than the polypeptide with respect to solubility, stability, and/or susceptibility to hydrolysis and proteolysis. See, for example, Morgan and Gainor, Ann. Rep. Med. Chem., 24:243-252 (1989). Examples of polypeptide mimetics are described in U.S. Pat. No. 5,643,873. Other patents describing how to make and use mimetics include, for example in, U.S. Pat. No. 5,786,322, 5,767,075, 5,763,571, 5,753,226, 5,683,983, 5,677,280, 5,672,584, 5,668,110, 5,654,276, 5,643,873 are all incorporated herein by reference in their entirety. Mimetics of the polypeptides disclosed herein may also be made according to other techniques known in the art. For example, by treating an GLP-1/Ex4 polypeptide of an embodiment of the disclosure with an agent that chemically alters a side group by converting a hydrogen group to another group such as a hydroxyl or amino group. Mimetics preferably include sequences that are either entirely made of amino acids or sequences that are hybrids including amino acids and modified amino acids or other organic molecules. An embodiment of the disclosure also includes hybrid GABAergic and incretin polypeptides, for example where a amoni acid is combined with a second nucleotide sequence.

In one embodiment, the amino-group can be replaced by halogen group, including but not limited to fluorine, chlorine, bromine, iodine, etc.

In one embodiment, the amino-group can be replaced by alkyl group, including but not limited to methyl group, ethyl group, propyl group, isopropyl group, butyl group, t-butyl group, pentyl group, hexyl group, heptyl group, etc. In one embodiment, the amino-group can be replaced by cycloalkyl group, including but not limited to cyclopentyl, cyclohexyl, and so on.

In one embodiment, the amino-group can be replaced by alkoxy group, including but not limited to alkoxy, methoxy, ethoxy, propyloxy, and so on.

In one embodiment, the amino-group can be replaced by alkenyl group, including but not limited to ethylene, propylene, and so on.

In one embodiment, the amino-group can be replaced by aryl group, including but not limited to phenyl group, naphthyl group, anthracenyl group, biphenyl group, pyrenyl group, perylenyl group, etc.

In one embodiment, the amino-group can be replaced by heteroaryl group, including but not limited to heteroaryl, pyridyl group, bipyridyl group, triazine group, acridyl group, thiophene group, imidazole group, oxazole group, thiazole group, triazole group, quinoliyl group isoquinoline group, and so on.

In another embodiment, the carbon-group can be replaced by a chaneical group including but not limited to aforementioned chemical groups. With chemical engineering techniques such chemical processing are well known in the art for chemical group modification or replacement.

In one embodiment, the activity of the composition of GABAergic and incretin is increased or decreased by carrying out selective site-directed mutagenesis. A DNA plasmid or expression vector containing the nucleic acid molecule or a nucleic acid molecule having sequence identity is preferably used for these studies using the U.S.E. (Unique site elimination) mutagenesis kit from Pharmacia Biotech or other mutagenesis kits that are commercially available, or using PCR. Once the mutation is created and confirmed by DNA sequence analysis, the mutant fusion protein is expressed using an expression system and its activity is monitored.

As aspect of the disclosure also includes the composition of GABAergic and incretin, preferably GABA, GABA synthesis enzyme GAD65, GAD67 and GLP-1 or Ex4 which have sequence identity at least about: >20%, >25%, >28%, >30%, >35%, >40%, >50%, >60%, >70%, >80% or >90% more preferably at least about >95%, >99% or >99.5%, to a sequence of an embodiment of the disclosure (or a partial sequence thereof). Identity is calculated according to methods known in the art. Sequence identity is most preferably assessed by the BLAST version 2.1 program advanced search (parameters as above). BLAST is a series of programs that are available online. The advanced blast search is set to default parameters. (ie Matrix BLOSUM62; Gap existence cost 11; Per residue gap cost 1; Lambda ratio 0.85 default). References to BLAST searches are: Altschul, S.F., Gish, W., Miller, W., Myers, E. W. & Lipman, D. J. (1990) "Basic local alignment search tool." J. Mol. Biol. 215:403_410; Gish, W. & States, D. J. (1993) "Identification of protein coding regions by database similarity search." Nature Genet. 3:266272; Madden, T. L., Tatusov, R. L. & Zhang, J. (1996) "Applications of network BLAST server" Meth. Enzymol. 266:131_ 141; Altschul, S.F., Madden, T. L., Schaffer, A. A., Zhang, J., Zhang, Z., Miller, W. & Lipman, D. J. (1997) "Gapped BLAST and PSI_BLAST: a new generation of protein database search programs." Nucleic Acids Res. 25:3389_3402; and Zhang, J. & Madden, T. L. (1997) "PowerBLAST: A new network BLAST application for interactive or automated sequence analysis and annotation." Genome Res. 7:649_656.

The term "isolated polypeptide" as used herein refers to a proteinaceous agent, such as a peptide, polypeptide or protein, which is substantially free of cellular material or culture medium when produced recombinantly, or chemical precursors, or other chemicals, when chemically synthesized.

The term "isolated nucleic acid" as used herein refers to a nucleic acid substantially free of cellular material or culture medium when produced by recombinant DNA techniques, or chemical precursors, or other chemicals when chemically synthesized. An "isolated nucleic acid" is also substantially free of sequences which naturally flank the nucleic acid (i.e. sequences located at the 5' and 3' ends of the nucleic acid) from which the nucleic acid is derived. The term "nucleic acid" is intended to include DNA and RNA and can be either double stranded or single stranded.

In one embodiment, the GABAergic disclosed herein includes but is not limited to GABA and GABA-synthesing enzyme glutamic acid, decarboxylase (GAD65).

GAD65 is an enzyme that is produced primarily by pancreatic islet cells. In mammals, GAD exists in two isoforms encoded by two different genes—Gad1 and Gad2. These isoforms are GAD67 and GAD65 with molecular weights of 67 and 65 kDa, respectively (Erlander M G, et al, 1991 Neuron 7:91-100). It is believed that GAD is one the best known targets of autoreactive T cells during the early phase of the autoimmune response (Kaufman et al. Nature 1993; 366:69). Although GAD65 has long been considered as a major target antigen for autoimmunity in T1D (Hinke, S. A. Endocrinology. 2007, 148, 4568-4571), the role of GAD65 in modulation of islet beta cell growth/proiferation, secretion and function are largely unknown. However depletion GAD positive islet beta-cells by autoimmune mechanisms could lead to low intra-islet GABA concentrations, and this would cause in an escalating cycle of beta-cell destruction. This hypothesis is supported by the finding that NOD mice expressing high levels of human GAD65 in their islets were protected against diabetes, but NOD mice expressing less GAD65 were not protected.

Furthermore, in embodiments, the composition of an embodiment of the disclosure may also be provided with cell stimulating agents as disclosed in U.S. Pat. No. 6,884,785 (herein incorporated by reference in its entirety) and commonly known by those skilled in the art to facilitate nucleic acid uptake. In additional embodiments, the composition of an embodiment of the disclosure may also be provided with cytokines as disclosed in U.S. Pat. No. 7,078,388 (herein incorporated by reference in its entirety) but not limited chemokine, interferon, interleukins and others well known by those skilled in the art to modify an immune response.

The composition of the disclosure in an embodiment provides for the expression of GABAergic and incretin and the incorporated DNA sequences (as a vaccine) with mutations that cause an amino acid change in a portion of the nucleotide vaccine sequence of which is not involved in providing activity or an amino acid change in a portion of the DNA vaccine involved in providing activity so that the mutation increases or decreases the activity of the DNA vaccination. The activity of the DNA vaccine is increased or decreased by carrying out selective site-directed mutagenesis. A DNA plasmid or expression vector containing the nucleic acid molecule or a nucleic acid molecule having sequence identity is preferably used for these studies using the U.S.E. (Unique site elimination) mutagenesis kit from Pharmacia Biotech or other mutagenesis kits that are commercially available, or using PCR. Once the mutation is created and confirmed by DNA sequence analysis, the mutant fusion protein is expressed using an expression system and its activity is monitored.

The disclosure also includes in an embodiment, a pharmaceutical composition, such as a prophylactic composition, for all the aforementioned uses. The pharmaceutical compositions of an embodiment of the disclosure are formulated to contain the described compositions or in a DNA vector form and can be administered to humans or animals by a variety of methods including, but not restricted to topical administration, oral administration, aerosol administration, intratracheal instillation, intraperitoneal injection, intravenous injection, intramuscular injection and gene therapy approach. Dosages to be administered depend on patient needs, on the desired effect and on the chosen route of administration. An example of a dosage of the composition for humans would be 0.01-10 mmol/kg:0.02 to 1000 nmol/kg of body weight (GABA:GLP-1/Ex4) or between about 0.002-2 mg/kg:0.2-1000 nmol/kg of body weight. (GABA:GLP-1/Ex4). Suitable concentrations of the DNA encoding the respective compound in composition for use may be about 1 μg/kg of body weight to 10 μg/kg of body or between 0.1 to 100 μg/kg of body weight. Suitable concentrations of the DNA vaccine for use comprise 0.1 to about 1000 microgram of DNA. The composition may also be introduced into cells using in vivo liposome or viral delivery vehicles. The numerous types of delivery vehicles suitable for use with an embodiment of the disclosure are well known to those skilled in the art. The compositions may be administered daily, weekly or as advised by a physician for as long as is required.

The compositions disclosed herein are useful alone, but may also be combined with other components such as a carrier or adjuvants in a pharmaceutical composition. The pharmaceutical compositions can be prepared by known methods for the preparation of pharmaceutically acceptable compositions which can be administered to patients, and such that an effective quantity of the nucleic acid or polypeptide molecule is combined in a mixture with a pharmaceutically acceptable vehicle. Suitable vehicles are described, for example in Remington's Pharmaceutical Sciences (Remington's Pharmaceutical Sciences, Mack Publishing Company, Easton, Pa., USA). On this basis, the pharmaceutical compositions could include an active compound or substance, such as a compound nucleic acid, polypeptide molecule or fusion protein, in association with one or more pharmaceutically acceptable vehicles or diluents, and contained in buffered solutions with a suitable pH and isoosmotic with the physiological fluids. The methods of combining the active molecules with the vehicles or combining them with diluents is well known to those skilled in the art. The composition could include a targeting agent for the transport of the active compound to specified sites within tissue.

The compositions described herein may be used in conjunction with any other known agents for treatment for type I and/or type II diabetes, such as for example with the use of diabetes medicaments and insulins. Diabetic medicaments may include for example Actos, Amaryl, avandia, DiaBeta, Diabinese, Dymelor, Glucophage, Glucophage XR, Glucotrol, Glucotrol XL, Glucovance, glynase, PresTab, Glyset, Micronase, Orinase, Pandin, Precose, Starlix and Tolinase. Suitable insulins include for example Aspart, Insulin Glargine (Lantus), Lente, Lispro (Humalog), NPH and Ultralente.

A subject for which an embodiment of the disclosure is suitable is any subject in need of such treatment which is one that is at risk for developing diabetes, a subject newly diagnosed with diabetes or a subject already diagnosed with diabetes. The methods and composition are relevant towards the treatment and/or prevention of type I diabetes as described herein. For example, such subjects may be a person with a genetic history of diabetes who has not yet developed diabetes or, who has newly diagnosed or diagnosed as diabetes. The subject may also be a person whose blood glucose is higher than average for that person's age and weight (normal blood glucose may be routinely determined from medical reference sources), although not high enough that the person is diagnosed diabetic. The subject may also be a person with a genetic history of diabetes who has not yet developed diabetes. Diabetes is diagnosed when the blood sugar levels are higher than an accepted normal range. According to ADA (American Diabetes Association) and CDA (Canadian Diabetes Association) standards, diabetes onset occurs when a subject has a fasting blood glucose level over 7.0 mmol/L, or a random (anytime of day) sugar that is greater than 11.1 mmol/L. Once diagnosed, any effort/means made to the patient, in order to combat the hyperglycemia, is treatment, rather than prevention. The compositions disclosed herein are administered to prevent and/or treat a subject with type I diabetes. Type I diabetes patient refers to a subject who usually has genetic predisposition or, who has insulitis beta-cell injury or, who has "pre"-diabetes with loss of first phase of insulin response, or a person who has been newly diagnosed diabetes. In newly diagnosed type I diabetes patients, as a result of the immune system attacking and destroying the insulin-producing islet beta-cells, their pancreas produce little or no insulin.

In one embodiment, that the administration of the combined composition of an embodiment of the disclosure can be also expressed in vivo directly using a gene therapy approach. These vectors have no infectious potential, provoke only mild local inflammatory reactions, and do not cause insertional mutagenesis. This prevents many of the drawbacks of viral gene therapy. This non-viral gene therapy is simpler and less expensive, and could be applied outside of a hospital setting by any physician. Co-administration of GABAergic and incretin through transferring of naked plasmid DNA following needle injection occurs more readily in skeletal muscle than in most other tissues (Wolff J A, et al, 1990 Science 247:1465-1468; Wolff J A, et al, 1991 Biotechniques 11:474-485). Moreover, transgene expression is generally much more prolonged than in other tissues, probably because striated myocytes are nondividing, long-lived cells. There is no obvious contra-indication for the use of these techniques in patients with autoimmune diseases, such as type I diabetes.

Taken together, a new method was developed using combined GABAergic and incretin for beta-cell regeneration and control of immunity at same time as a novel therapy for the prevention and treatment of type I diabetes. This combined therapy provides reciprocity effect on islet beta-cell regeneration and suppression of islet autoimmunity. The remarkable improved efficacy has proved by these in vivo studies in multiple-low-dose-streptozotocin (MLDS)-induced diabetes CD1 mice (a model of beta-cell injury) and in T1D-prone non-obese diabetes (NOD) mice or in transgenic TCR NOD mice. The combined GABAergic and incretin therapy which is exemplified by GABA and GLP-1/Ex4 in embodiment of the disclosure achieved complete remission in NOD mice after onset of diabetic hyperglycemia. The complete remission of diabetes in a established diabetic subject is however never be achieved by either GABA treatment alone or GLP-1/Ex4 treatment alone in a established T1D. Therefore, an embodiment of the disclosure provide an effective new therapy for the prevention of T1D and for the treatment of T1D after onset on diabetic hyperglycemia in a subject.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The following non-limiting examples are illustrative of the present disclosure:

EXAMPLES

Example 1

As shown in the FIG. 1, the diabetes induction by multiple-low-dose-streptozotocin (i.p. 40 mg/kg for four consecutive days, MLDS) in mice can be prevented by daily injection of GABA. The MLSD murine model is commonly used for study of T1D (Rossini A A et al, 1978 Nature. 276(5684): 182-4; Harlan D M et al, 1995 Diabetes 44(7):816-23) in which the beta-cells are destroyed by the toxic streptozotocin that leads to insulin insufficiency. To certain extent, T-cell mediated beta-cell inflammation (insulitis) is found in the multiple-low-dose streptozotocin induced diabetic hyperglycemia. However, insulitis may not be necessary occurred in the hyperglycemic mice induced by one injection of streptozotocin of high dose (i.e. 200-250 mg/kg), as in the latter case the beta-cell are rapidly destroyed. Therefore, MLDS is a model of beta-cell injury, to certain degree insulitis, but an ideal autoimmune disease model (Gerling I C et al, 1994 Diabetes; 43, 433; Giarratana N et al, 2007 Methods Mol Biol. 380:285-311. Daily intraperitoneal injection of GABA (20 g/mouse) prevented development of diabetic hyperglycemia in MLDS CD1 mice (FIG. 1A). Under present experimental conditions, 100% of control mice (8 of total 8) developed diabetic hyperglycemia after 7-day MLDS injection, however, only one GABA treated SZT mice developed overt hyperglycemia that contributed to overall slightly increased mean value of blood glucose levels compared to those mice prior to the drug-injection (FIG. 1A). GABA has no effect on the glucose tolerance in normal mice as determined by intraperitoneal glucose tolerance test (IPGTT) 7 days before STZ injection. While non-treated MLDS mice displayed severe impaired glucose tolerance, GABA treated MLDS-mice showed significant improved glucose tolerance of which close to the IPGTT measured from the mice before STZ-injection shown in dashed-line (FIG. 1B,1C). GABA treatment does not alter the insulin sensitivity (FIG. 1D) but significantly improved glucagon tolerance in MLDS-mice (FIG. 1E, F). These results suggest that GABA exerts its action preferably at the insulin production site rather than the peripheral insulin action site. GABA treated MLDS-mice showed elevated circulating insulin (FIG. 1G) and reduced serum glucagon levels (FIG. 1H) that leads to increased ratio of insulin to glucagon levels (FIG. 1I). Overall, daily GABA injection prevented diabetic hyperglycemia and maintained close to normal glucose tolerance in the MLDS-mice over the course of 53 days after the toxic drug injection.

Treatment of GABA does not make a statistically difference on the bodyweight and food intake between non-treated and GABA-treated groups (FIG. 2A-C), treatment of GABA significantly improved diabetic symptoms such as polydipsia and polyuria (Fig D, E). These results are supported by the findings that saline-treated MLDS mice displayed severe sickness, whereas diabetic sickness is not found in any mouse from GABA treated group throughout the feeding course.

Figure 2:
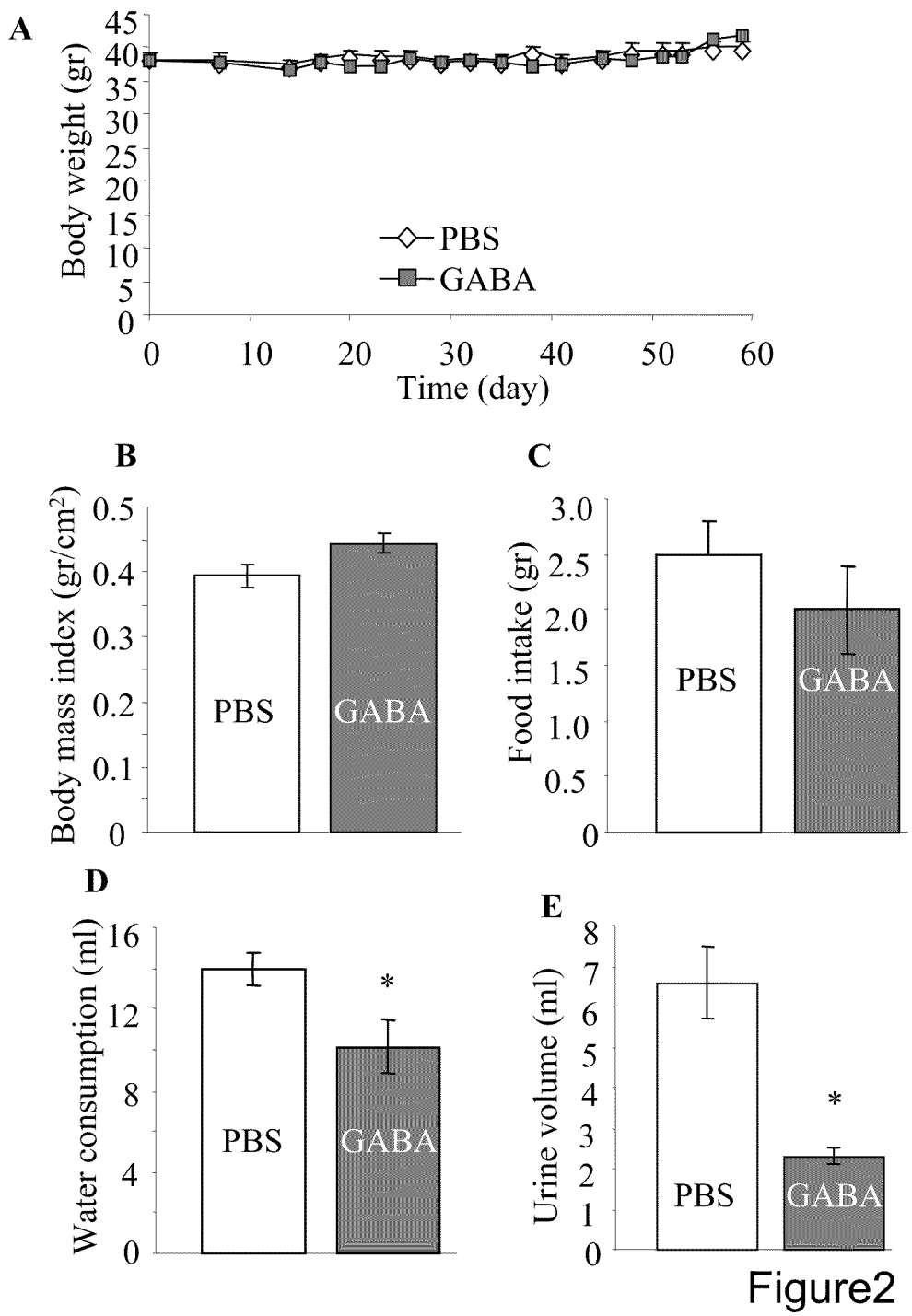
FIG. 2 A-E show that GABA significantly improves diabetic symptoms in MLDS mice. Although the body weight and the food intake were significantly different between the two groups (A-C), treatment of GABA significantly improved diabetic symptoms such as polydipsia and polyuria (D, E). At the end of the experiments, saline-treated MLDS mice displayed severe sickness which was not found in any mouse from GABA treated group.

To determine the mechanism underlies GABA effect on prevention diabetic hyperglycemia and improved circulating insulin levels and reduced glucagon levels, pancreatic immunohistochemistry was conducted in the MLDS-mice. It was found that the beta-cells were largely destroyed in non-treated MLDS-mice that left the remaining islets with padding of numerous alpha-cells (FIG. 3A); however, treatment of GABA significantly reserved the beta-cell mass with significantly reduced alpha-cell mass when compared to non-treated MLDS-mice (FIG. 2A-C). The reserved beta-cell mass in GABA treated MLDS-mice is found to be associated with significant reduction of insulitis as scored by HE staining for infiltrated lymphocytes in the islets (not shown).

Figure 3:
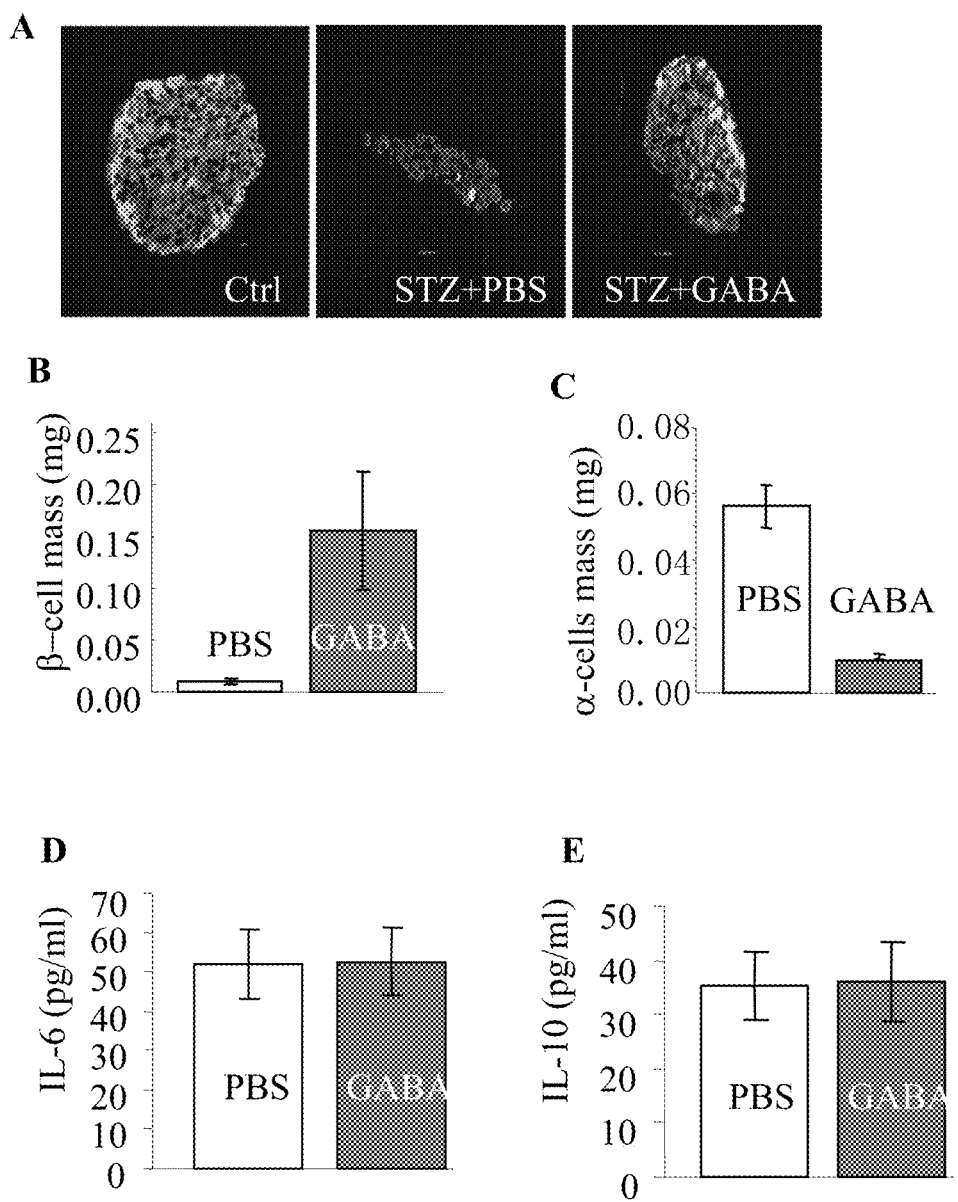
FIG. 3 A-I show GABA preserves islet beta-cell mass which is associated with reduced circulating inflammatory cytokines in MLDS mice. The pancreatic immunohistochemistry shows that the beta-cells were largely destroyed in saline-treated MLDS-mice that left the remaining islets with padding of numerous alpha-cells (A); Treatment of GABA significantly reserved the beta-cell mass and significantly reduced alpha-cell mass (A-C). The serological studies using Multiplex Bead-Based Cytokine Assay was performed to examine. circulating cytokine levels. It was showed that while the serum levels of IL-6 and Th2 cytokine IL-10 were not different between the two groups (D, E), the circulating levels of pro-inflammatory IL-1-beta (F) and TNF-alpha (G) were significantly decreased in the GABA-treated MLDS-mice. GABA treatment also significantly reduced circulating inflammatory cytokines IL-12 (H) and INF-gamma (I).
Figure 3:
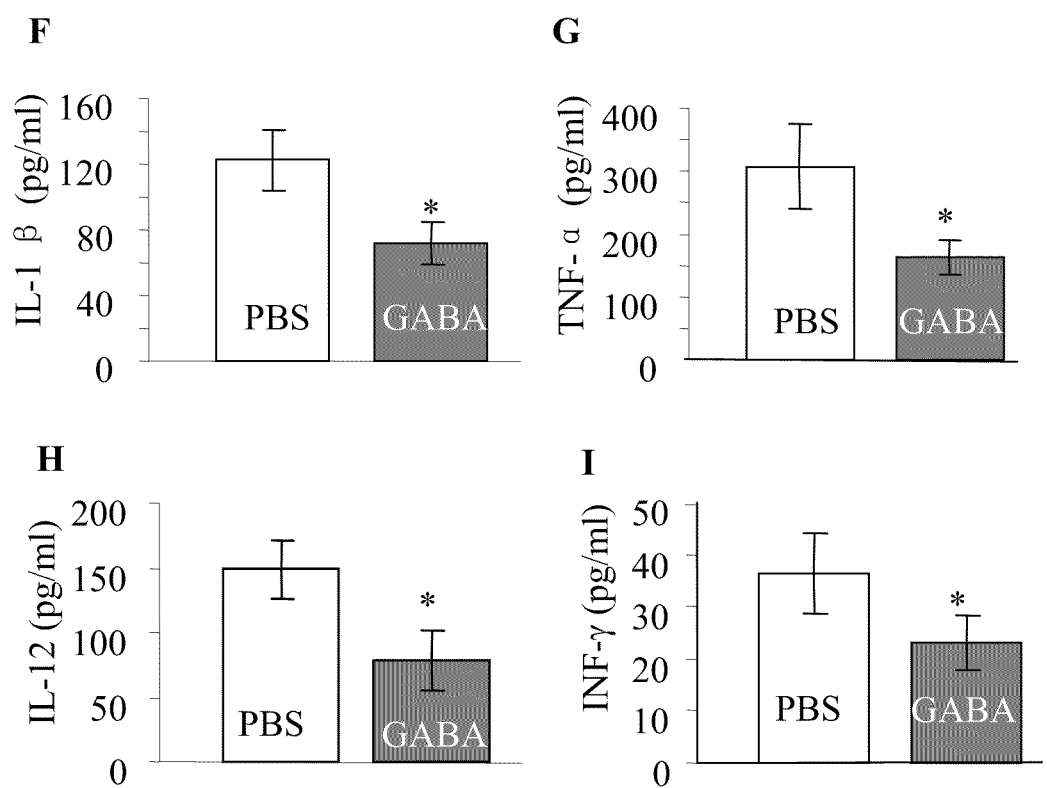

Given that the cytokines play important roles in autoimmune diabetes, the circulating cytokine levels in GABA or non-GABA treated MLDS-mice were examined. The serological studies showed that while the serum levels of IL-6 and Th2 cytokine IL-10 were not different between the two groups (FIG. 3D, 3E), the circulating levels of pro-inflammatory IL-1 (FIG. 3F) and TNF-alpha (FIG. 3G) were significantly decreased in the GABA-treated MLDS-mice. Furthermore, GABA treatment also significantly reduced circulating inflammatory cytokines including IL-12 (FIG. 3H) and INF-gamma (FIG. 3I). These results suggest that GABA has anti-inflammatory effects in MLDS-mice through blockage of inflammatory cytokines and prevention MLDS-induction of diabetes via reducing islet immune cell infiltration (Martin, et al. 2007, 4623).

Figure 4:
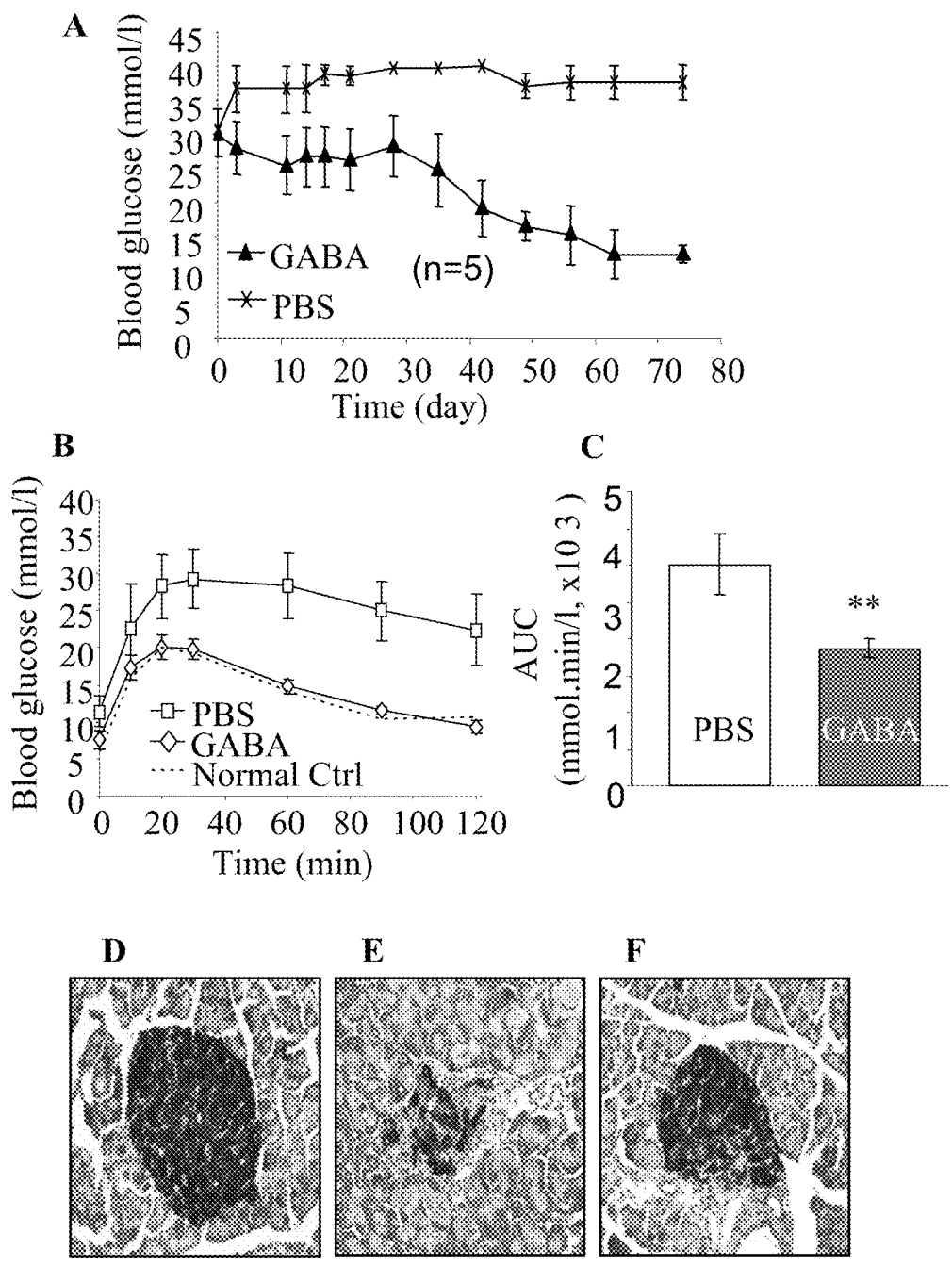
FIG. 4 A-K show treatment of GABA reverses MLDS-induced diabetic hyperglycemia (A) with improved glucose tolerance (B, C). Treatment of GABA significantly restored beta-cell mass and reduced alpha-cell mass (D-H). This leads to consequent elevated circulating insulin (I) and reduced circulating glucagon levels (J). The ratio of insulin to glucagon is significantly increased (K).
Figure 4:
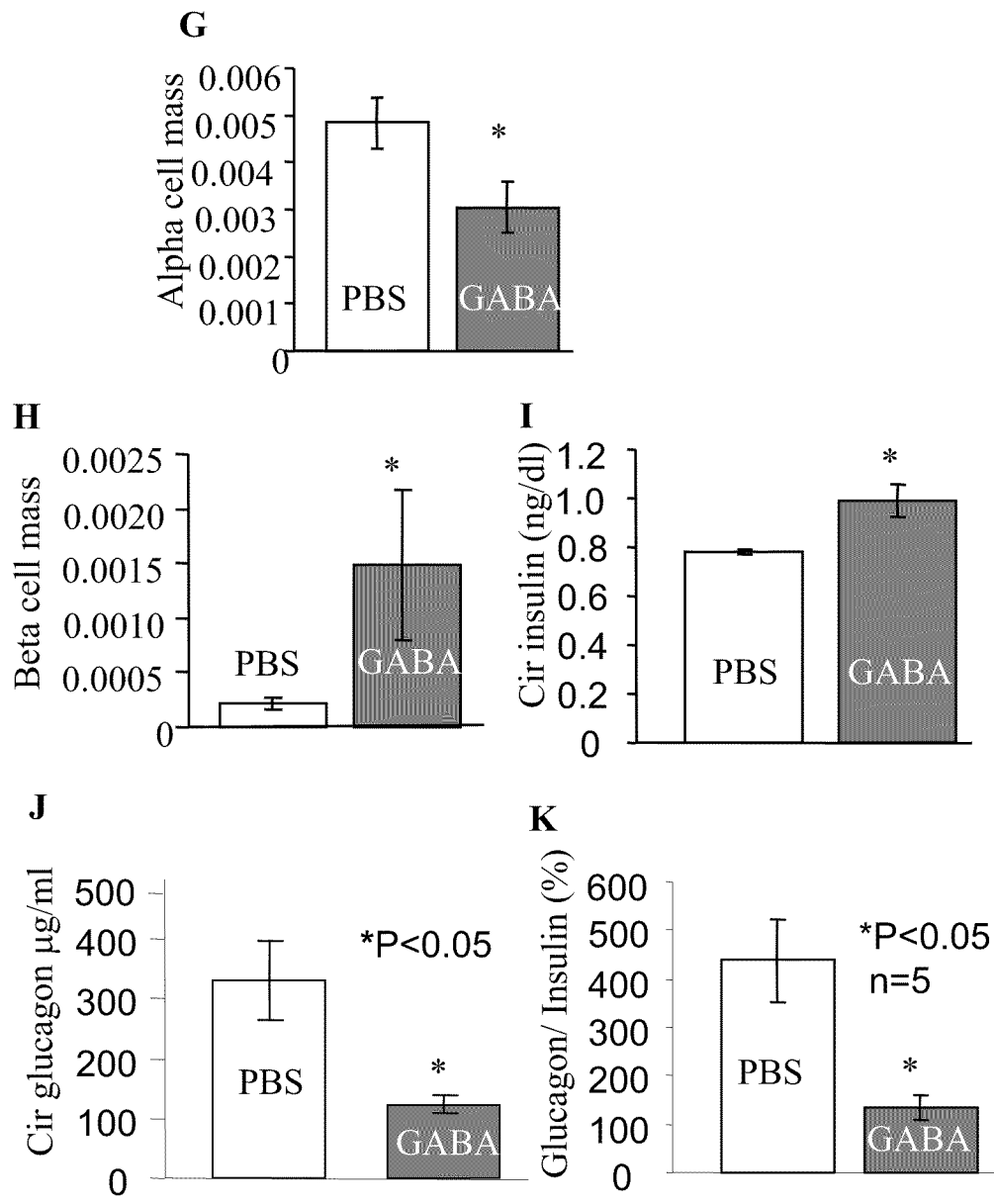

To investigate if GABA can reverse diabetes, daily GABA injection was started in well established diabetes in MLDS-mice (blood glucose>30 mM). It is observed that the blood glucose started to decline only a few days after GABA injection (FIG. 4A). The blood glucose levels were steadily decline along with improved glucose tolerance during the course of experiment. At the day 74 after GABA daily administration, while the blood glucose levels were closed to the normal range (FIG. 4A), the glucose tolerance was almost identical to control normal mice (FIG. 4B), indicating after more than two month treatment with GABA diabetes in these MLDS-mice were reversed.

Islet histochemical studies were performed to determine if GABA has protective effects on the islets in established diabetes mice. It was found that compared to the islets of control mice (FIG. 4D) the beta-cells in non-treated MLDS-mice were severely destroyed and the remaining islets were stuffed with large numbers of alpha-cells and surrounded with large number of lymphocytes (FIG. 4E). In a contrary, the GABA-treated MLDS-mice displayed almost normal islet morphology with significant enlarged beta-cell mass and reduced alpha-cell mass (FIG. 4F-H). Notably, few lymphocytes were seen in the islets of GABA-treated MLDS-mice (FIG. 4F). Enhanced beta-cell mass and reduced alpha-cell mass in GABA-treated MLDS-mice was found to be associated with elevated circulating insulin (FIG. 4I) and reduced glucagon (FIG. 4J) levels. This led to a largely increased ratio of insulin to glucagon (FIG. 4K). These data indicate the effects of GABA on reversing diabetes in LMDS-mice are associated with reduced islet inflammation, enlarged beta-cell mass and enhanced beta-cell function.

Figure 5:
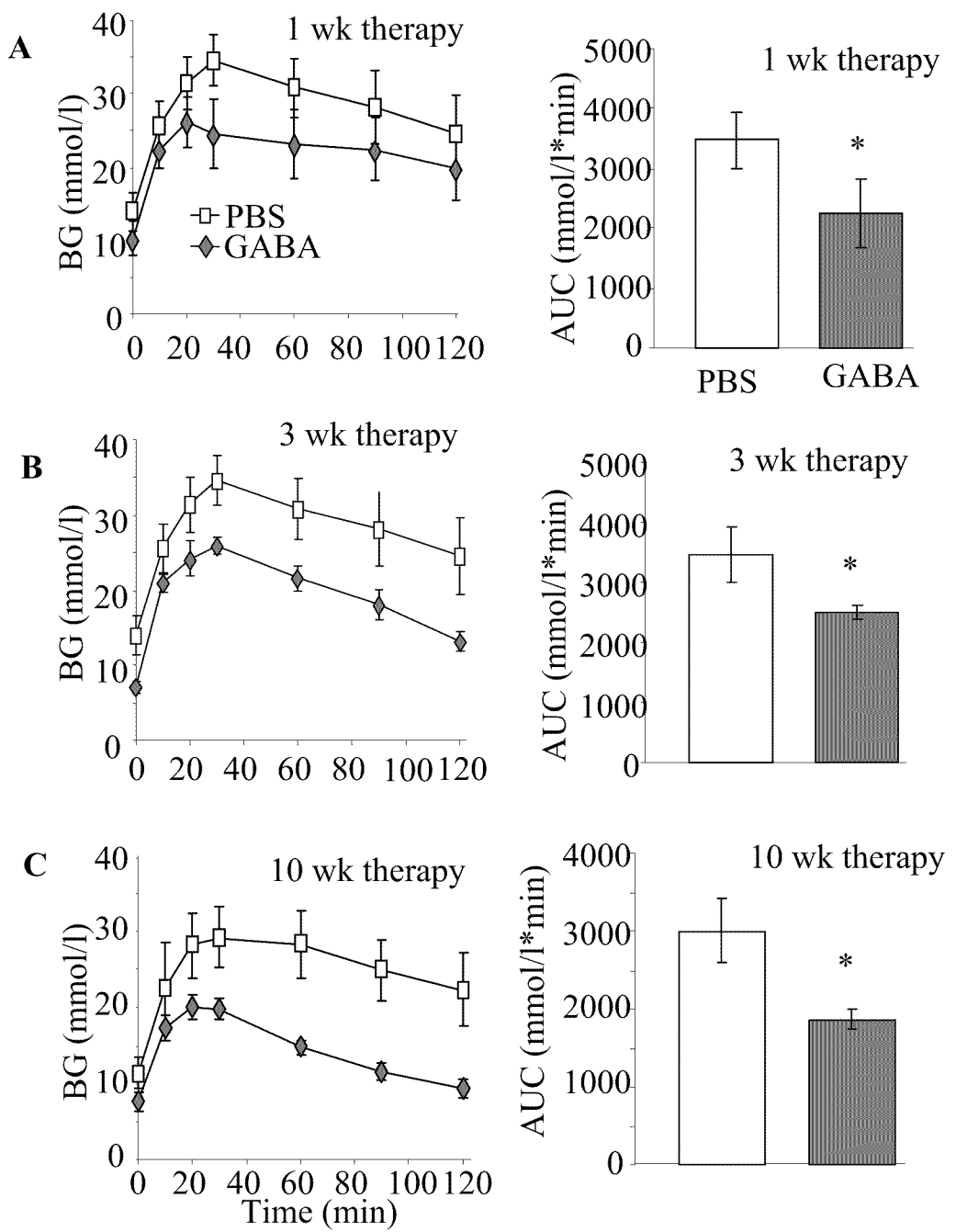
FIG. 5 A-F show GABA improves glucose tolerance and metabolic symptoms in established diabetic MLDS mice. The Intra-Peritoneal Glucose Tolerance Test (IPGTT) was performed at 7th days after GABA injections and improved glucose tolerance was seen in GABA-treated MLDS-mice (A, A'). GABA treatment steadily improves glucose tolerance in the MLDS mice at all time points examined including two weeks and eight weeks after GABA injections (B-C). The reversed diabetes in MLDS mice is also evident by normalized metabolic status as determined by metabolic studies (D-F).
Figure 5:
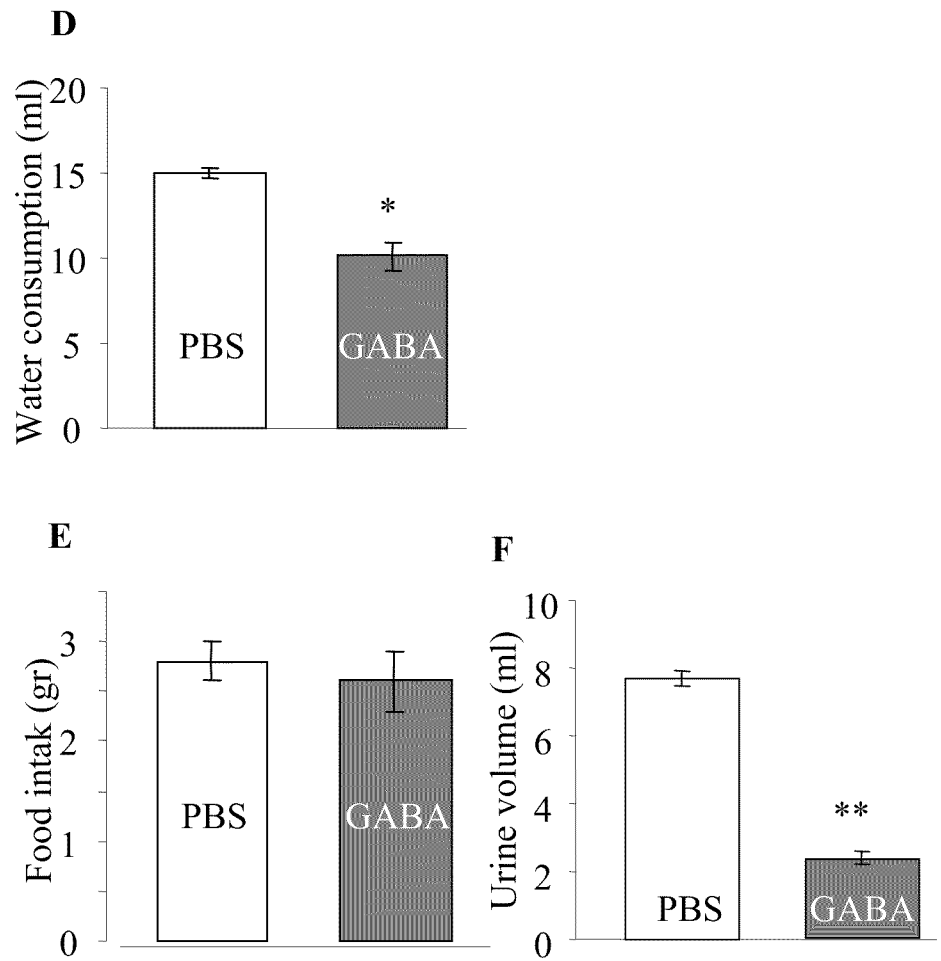

The therapeutic efficacy of GABA is effective rapidly in the MLDS-mice which is exemplified by improved glucose tolerance in GABA-treated mice immediately after GABA therapy. As a demonstration of the IPGTT performed at 7th days after GABA injections, the glucose tolerance has been already significantly improved (FIG. 5A, 5A'). GABA treatment steadily improves glucose tolerance in established diabetic MLDS mice at all time points examined including two weeks and eight weeks after GABA injections (FIG. 5B-5C). In a good agreement with improved glucose tolerance, GABA-treated MLDS-mice displayed normalized metabolic conditions as demonstrated by metabolic studies (D-F).

These results suggest that effect of GABA in preventing and reversing MLDS-induced murine diabetic hyperglycemia is likely via its dual actions involving islet beta-cell mass expansion and suppression of islet beta-cell autoimmunity. Given that MLDS is not an autoimmune disease model and the MLDS-induced diabetic hyperglycemia may be also partially contributed by direct drug toxic effect on the beta-cells that causes beat-cell apoptosis/necrosis, the non-obese diabetic (NOD) mice were used to verify the protective and therapeutic effects of GABA in diabetes. NOD mouse develops spontaneous autoimmune diabetes which shares histoimmunological, serological and clinical features with T1D in humans (Tisch R, McDevitt H 1996 Cell. 3; 85(3):291-7.; Atkinson and Leiter 1999 Nat Med. 5(6):601-4.).

Figure 6:
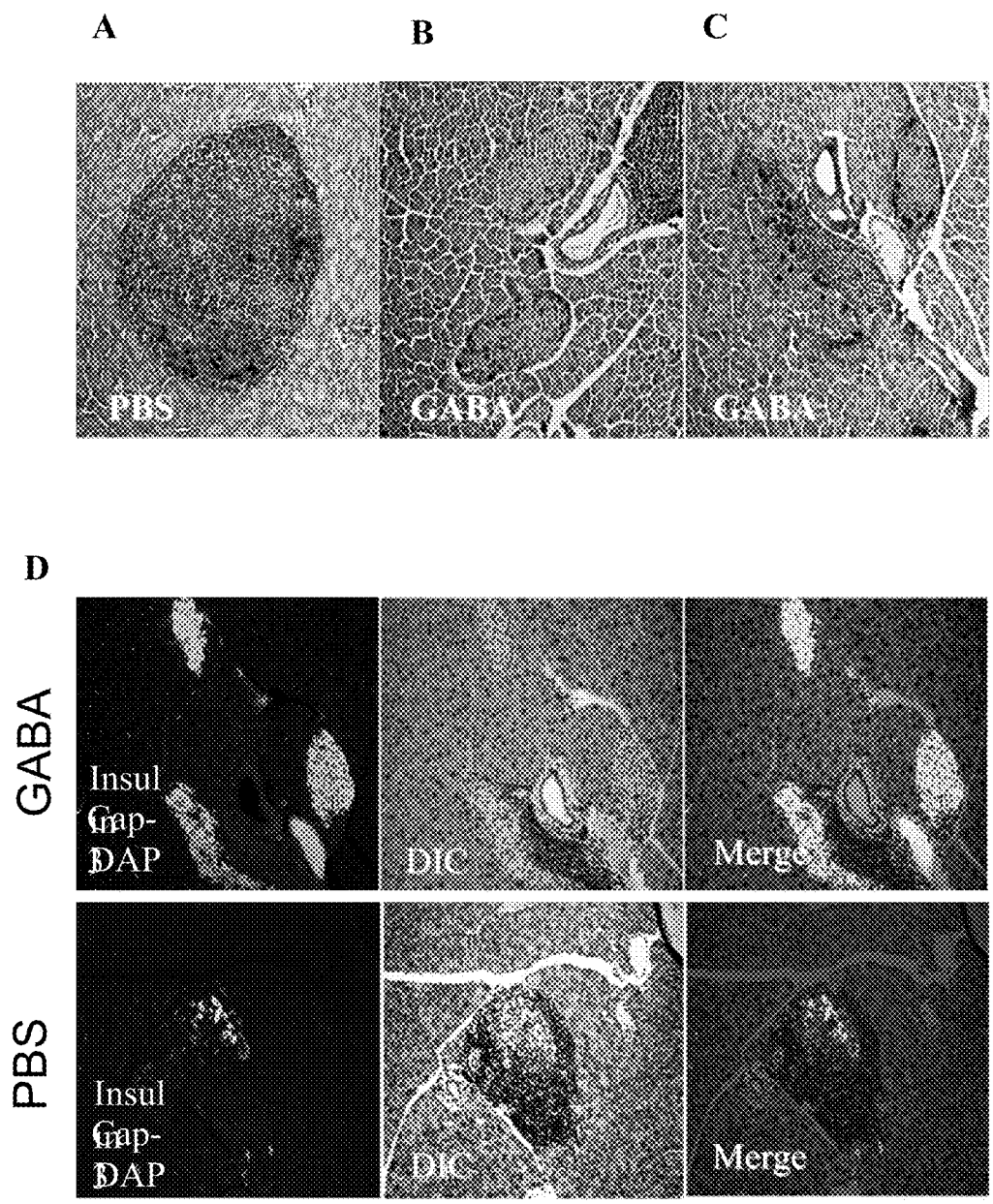
FIG. 6 A-J show GABA prevents onset of diabetes in non-obese diabetes (NOD) mice. Islet histochemistry was performed at the age of 13 weeks before the obvious onset of diabetic hyperglycemia and it showed severe insulitis were found in some non-treated NOD mice (A) but not in the GABA-treated NOD mice (B, C). Islet histochemistry using anti-caspase-3 antibody was performed to determine the rate of beta-cell apoptosis (D). After age of 18 weeks, the non-treated NOD mice developed severe hyperglycemia but the GABA-treated NOD mice kept lower blood glucose levels (E). The saline-NOD mice developed impaired glucose tolerance but not the GABA-treated NOD mice (F, G). GABA treatment significantly increased circulating C-peptide (H) and reduced glucagon levels (I) in the NOD mice. The treatment of GABA significantly elevated the ratio of insulin to glucagon (J).
Figure 6:
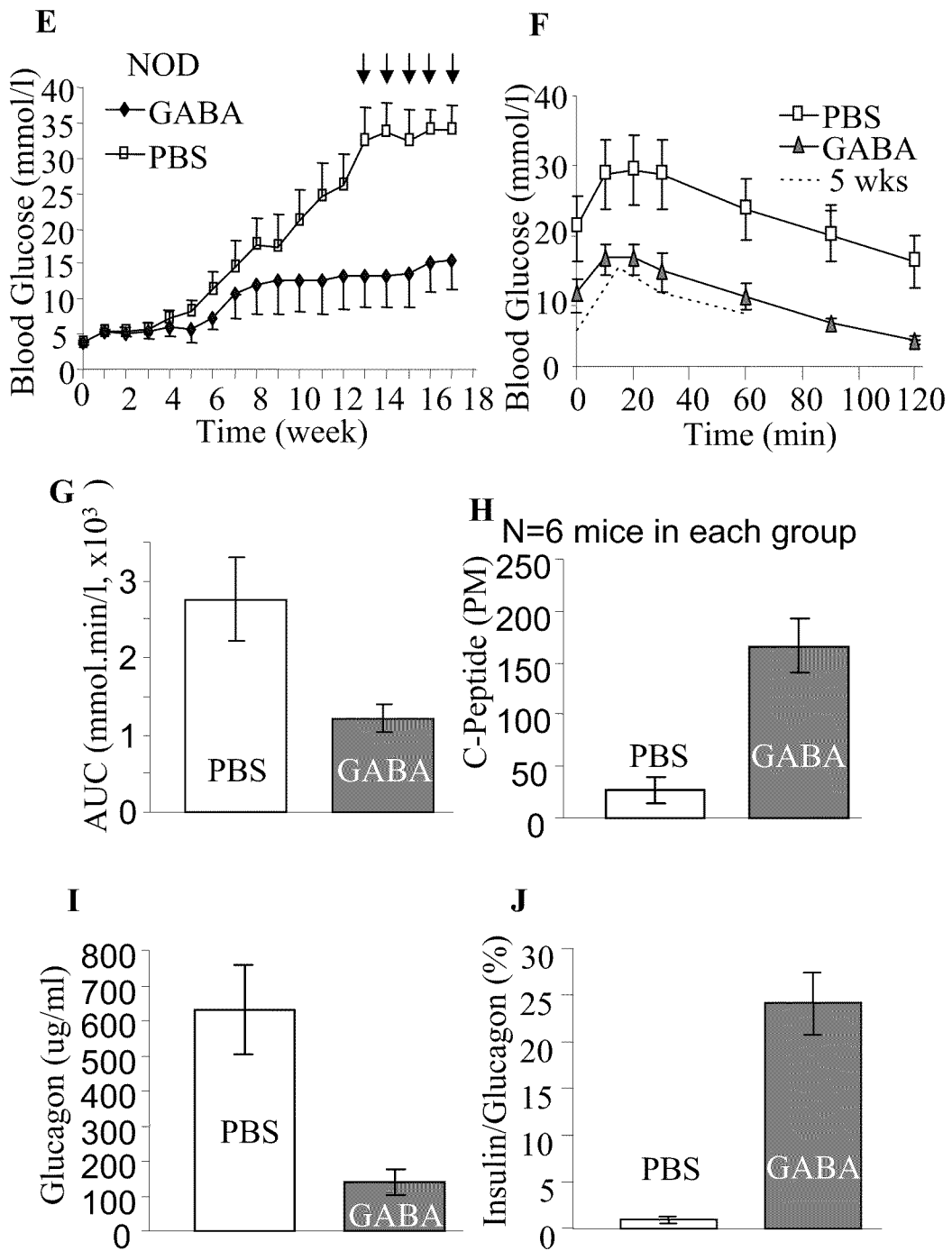
Figure 7:
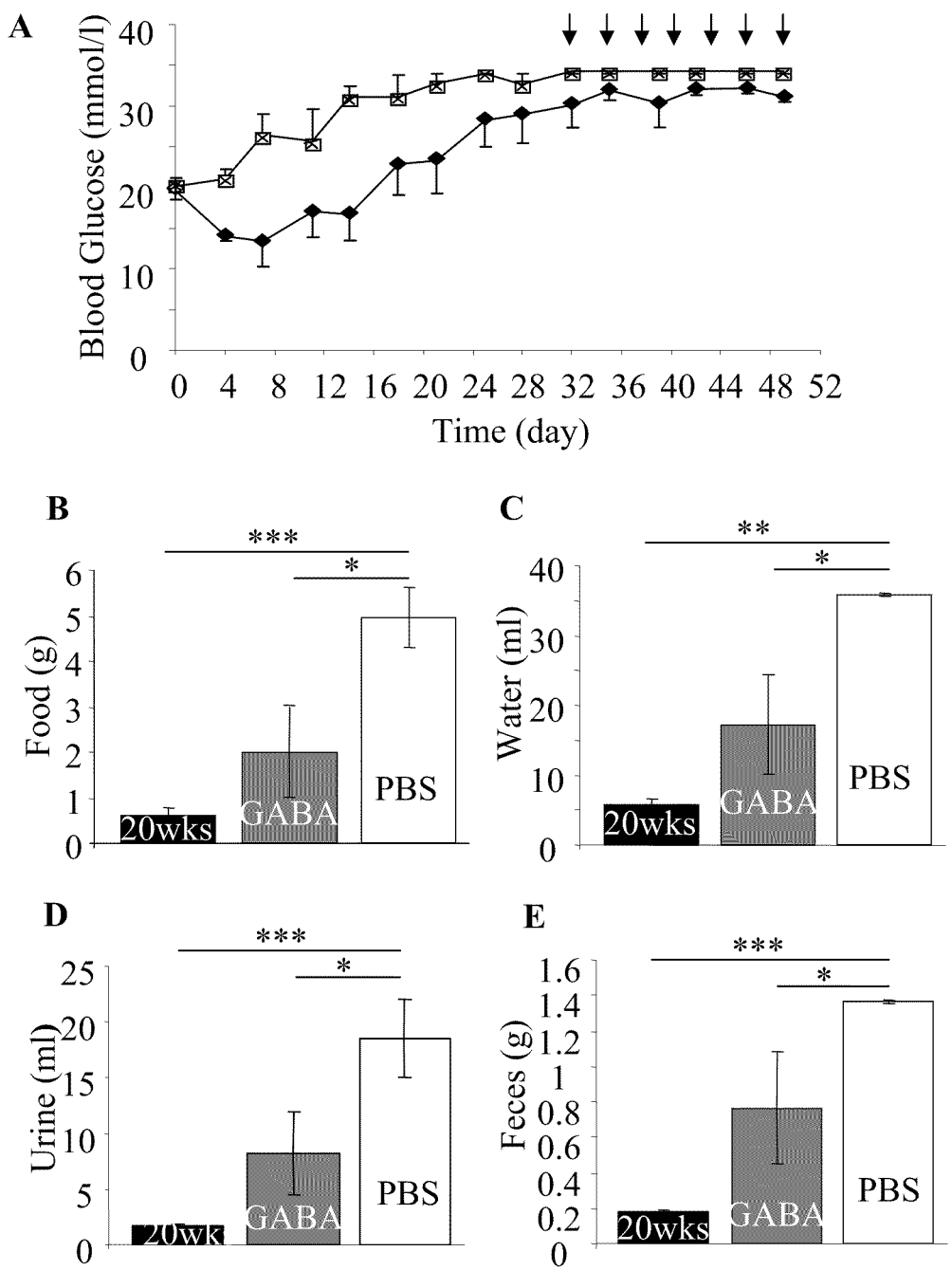
FIG. 7 A-E show the effects of GABA in reversing diabetes in established diabetes in NOD mice. GABA treatment significantly reduced blood glucose levels in established diabetic hyperglycemic NOD mice (A). However, these effects are transient that indicating that GABA alone is not effective in completely reversing diabetic hyperglycemia in autoimmune NOD mice. Nevertheless, GABA treatment significantly improved metabolic status in established diabetic NOD mice which is exemplified with, in particular, reduced food intake (B) and water consumption (C) and reduced urine (D) and feces (E).

To examine the role of GABA in the development of diabetes in NOD mice, GABA daily injections were started at age of 5 week and PBS injections as control. Islet immunohistochemistry was performed at their age of 13 wks before the onset of obvious diabetic hyperglucemia. The obvious insulitis was detected in PBS-NOD and the insulitis score showed that only about 10% islets appeared normal morphology and >70% islets were infiltrated with various degree of lymphocytes of which about 20% islets displayed severe insulitis where about >90% islets areas were occupied by lymphocytes (FIG. 6A). In contrast, in GABA-treated NOD mice about >70% islets showed normal morphology without lymphocyte infiltration (FIG. 6B); no severe insulitis was seen in this group in which the affected islets were mostly periphery and only about 15% islets showed relatively severe insulitis where about 20-30% islets areas were occupied by lymphocytes (FIG. 6C). These results indicate that GABA has anti-inflammatory effects in preventing the development of insulitis in the NOD mice. Islet histochemistry using anti-caspase-3 antibody showed that the beta-cell apoptosis was reduced in GABA-treated NOD mice (FIG. 6D). At 18 wks of age, the saline-treated NOD mice developed severe diabetic hyperglycemia but the GABA-treated NOD mice kept lower blood glucose levels (FIG. 6E). It is noted that beyond this age, the blood glucose levels of saline-treated NOD mice were out of the scale of the measurement (red arrows FIG. 6F). These non-treated NOD mice also developed impaired glucose tolerance (FIG. 6F, 6G), associated with reduced circulating C-peptide (FIG. 6H) and elevated circulating glucagon levels (FIG. 6I). In addition, these untreated NOD mice displayed severe sickness and the daily insulin-injections were required to maintain their lives. In contract, while the GABA-treated mice kept relatively constant glucose levels, although higher than those measured at their earlier ages (FIG. 6E), they showed morphologically normal, without any diabetic sign and close to normal glucose tolerance (FIG. 6F, 6G). The circulating C-peptide and glucagon levels were close to those measured at their earlier age (5 wks) (FIG. 6E, 6F). The treatment of GABA significantly elevated the ratio of insulin to glucagon (FIG. 6J). These results suggest that GABA significantly prevented development of severe diabetic hyperglycemia in NOD mice.

To investigate if GABA has effects on established diabetes in NOD mice, the diabetes hyperglycemic NOD mice were divided into two groups and treated with GABA or PBS. As shown (FIG. 7A), the blood glucose levels of PBS-treated NOD mice were steadily increased during the subsequent feeding course, however, the treatment of GABA reduced glucose levels significantly immediately after starting the injection and maintained at the lower levels. It is noticed that when the blood glucose levels of the PBS-NOD mice beyond the scale of the measurement (red arrows FIG. 7), the mice displayed severe sickness and started to die if daily insulin injections were not given. In contrast, treatment of GABA significantly reduced hyperglycemia in NOD mice and maintained lower blood glucose levels for about two weeks. The blood glucose of GABA-treated mice started to climb up and became hyperglycemic eventually. However, no obvious sickness was developed in this GABA-treated group. The metabolic studies indicated that the diabetic symptoms were significantly lessened in GABA-treated mice (FIG. 7B-E).

These results indicate that GABA alone has a transient effect on reversing diabetic hyperglycemia in established diabetic NOD mice while ameliorating diabetes throughout the course of the experiments.

Figure 8:
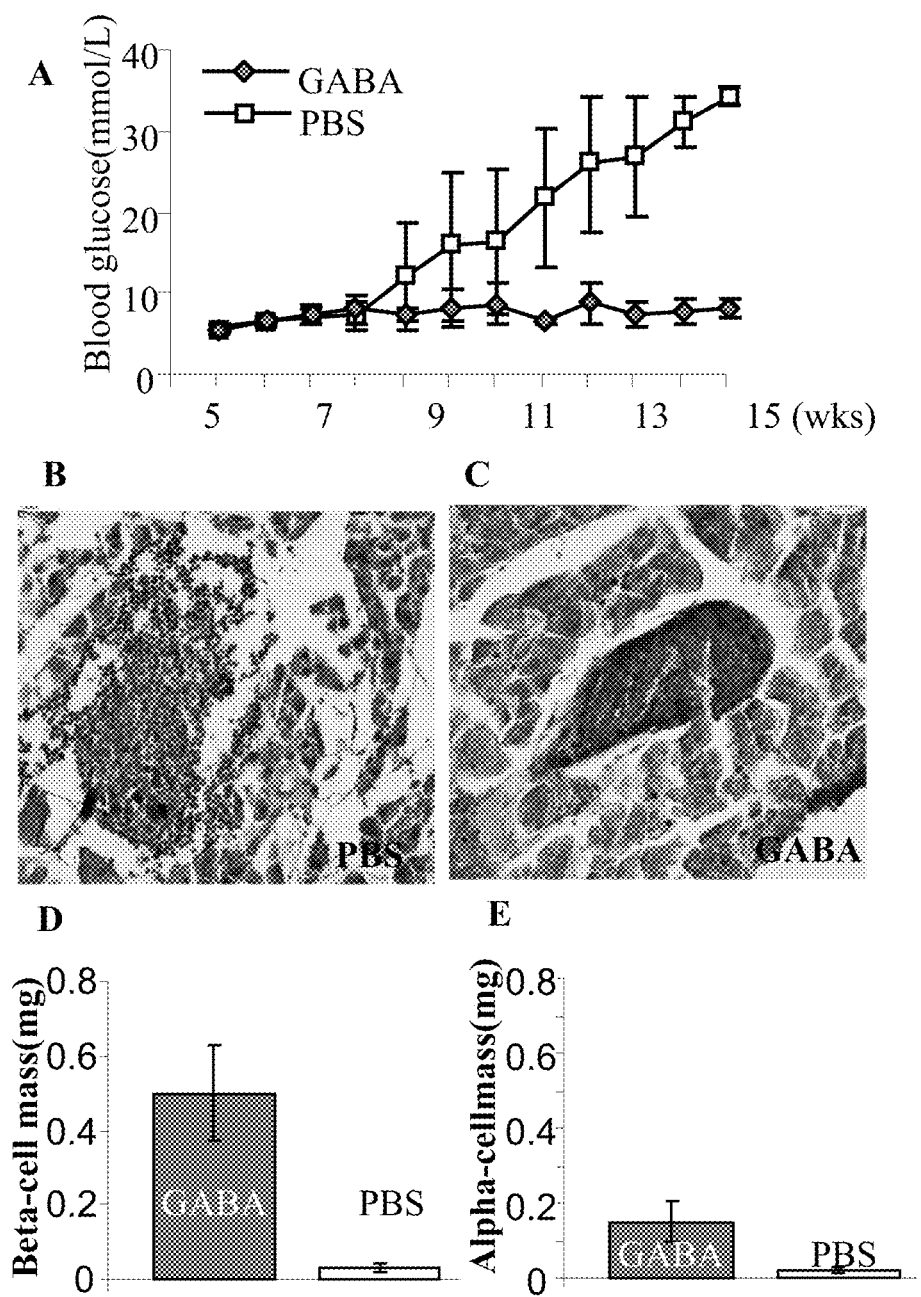
FIG. 8 A-E show that GABA prevents diabetes onset in TCR-NOD mice through inhibition of T-cell mediated islet destruction. Daily injection of GABA completely prevents diabetic hyperglycemia in transgenic TCR-NOD mice (A). Pancreatic histochemistry shows severe T-cell infiltration in islets of non-treated TCR-NOD mice (B), which was obviously diminished in the GABA-treated mice TCR-NOD mice (C). The beta-cell mass (D) and alpha-cell mass (E) are largely reserved in the mice treated with GABA.

TCR NOD mice were used to investigate the potential role of GABA on the T-cell function. The 8.3-TCR NOD mouse is a severe T1D mouse model (Amrani A et al, 1999 Clin Invest. 103(8):1201-9) and developed diabetic hyperglycemia at about age of 11 wks (FIG. 8A). Autoimmune diabetes in NOD mice results from destruction of pancreatic b-cells by T lymphocytes. The CD8+ cytotoxic T lymphocytes is thought to be the initial beta-cell insult in diabetes in which the initiation is a Fas-dependent process (Amrani A et al, 1999 Clin Invest. 103(8):1201-9). The 8.3-TCR NOD mouse monoclonal T-cells bearing a T-cell receptor (8.3-TCR) that is representative of TCRs used by CD8+ cytotoxic T lymphocytes propagated from the earliest insulitic lesions of NOD mice. Previous studies showed that the diabetogenic CD8+ cytotoxic T lymphocytes representative of cytotoxic T lymphocytes involved in the initiation of autoimmune diabetes (Amrani A et al, 1999 Clin Invest. 103(8):1201-9). Remarkably, compare to the saline-treated mice, GABA treatment completely prevented the development of diabetic hyperglycemia in these 8.3-TCR NOD mice (FIG. 8A). Islet studies showed that PBS-treated mice developed severe lymphocytes infiltration in pancreatic islets (FIG. 8B), which was dramatically blocked upon GABA treatment. The islet mass was largely reserved in the GABA-treatment mice (FIG. 8D, 8E). These data indicate that GABA may exert direct effects on suppression of diabetogenic CD8+ cytotoxic T lymphocytes.

Figure 9:
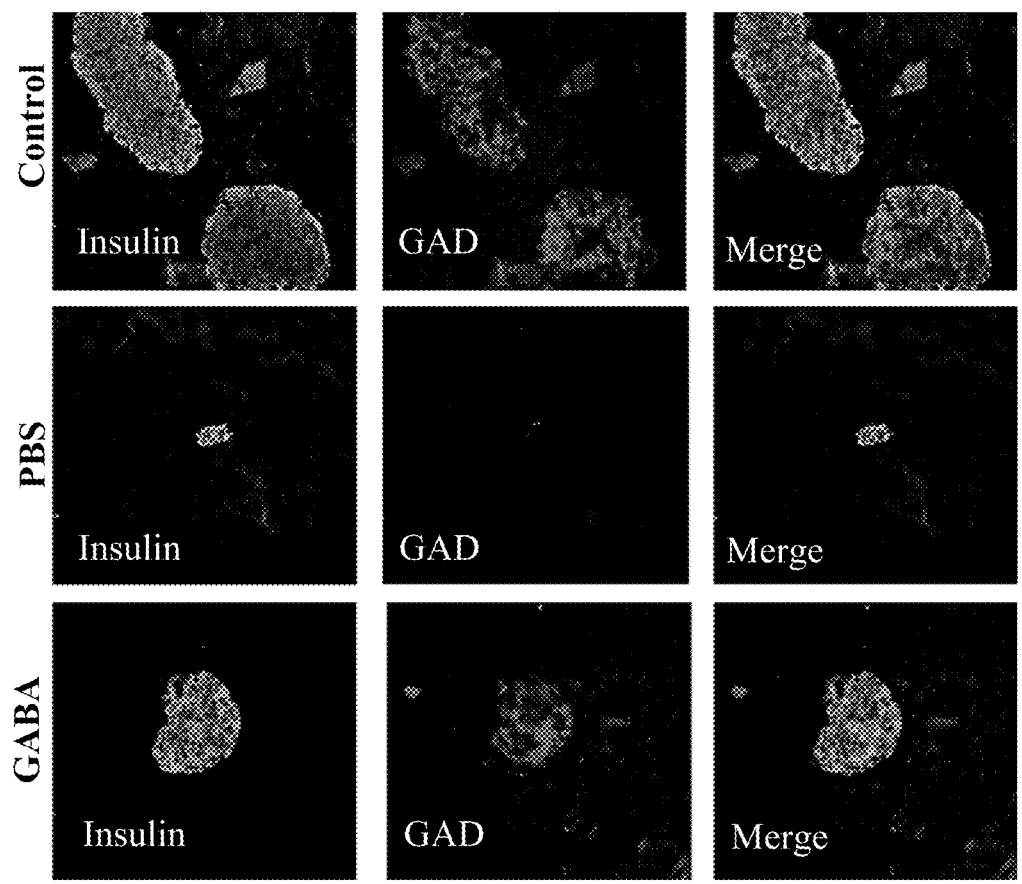
FIG. 9 shows GABA reserves insulin and GAD65/67 content in TCR-NOD mice. The Shown is pancreatic staining of insulin and GAD65/67 of control mice, non-treated TCR-NOD mice and GABA-treated TCR-NOD mice.

GAD65 has long been considered as a major antigen initiating the pathogenesis in T1D. Given that the protective effects of GABA in the development of diabetes in the diabetic animal models, I proposed that as the rate limiting enzyme of GABA synthesis, GAD has important role in maintaining islet function. To determine if treatment of GABA has effects on the expression levels of GAD65, we performed pancreatic GAD staining in the TCR transgenic NOD mice. The results showed that prior the onset of diabetes, the GAD65 were found to be highly expressed within the islet beta-cells (FIG. 9A top); in contrast, in the non-treated NOD mice that developed severe diabetic hyperglycemia there was no GAD65 staining at all found in entire pancreatic sections from all the mice examined (FIG. 9A middle), whereas treatment of GABA largely reserved the islet beta-cell mass and the intact association with GAD65 (FIG. 9, bottom). These findings indicate that the expression levels of endogenous GAD65 is positively proportional to the islet beta-cell mass suggesting that the endogenous GABA is important in maintaining islet cell function under normal conditions.

Figure 10:
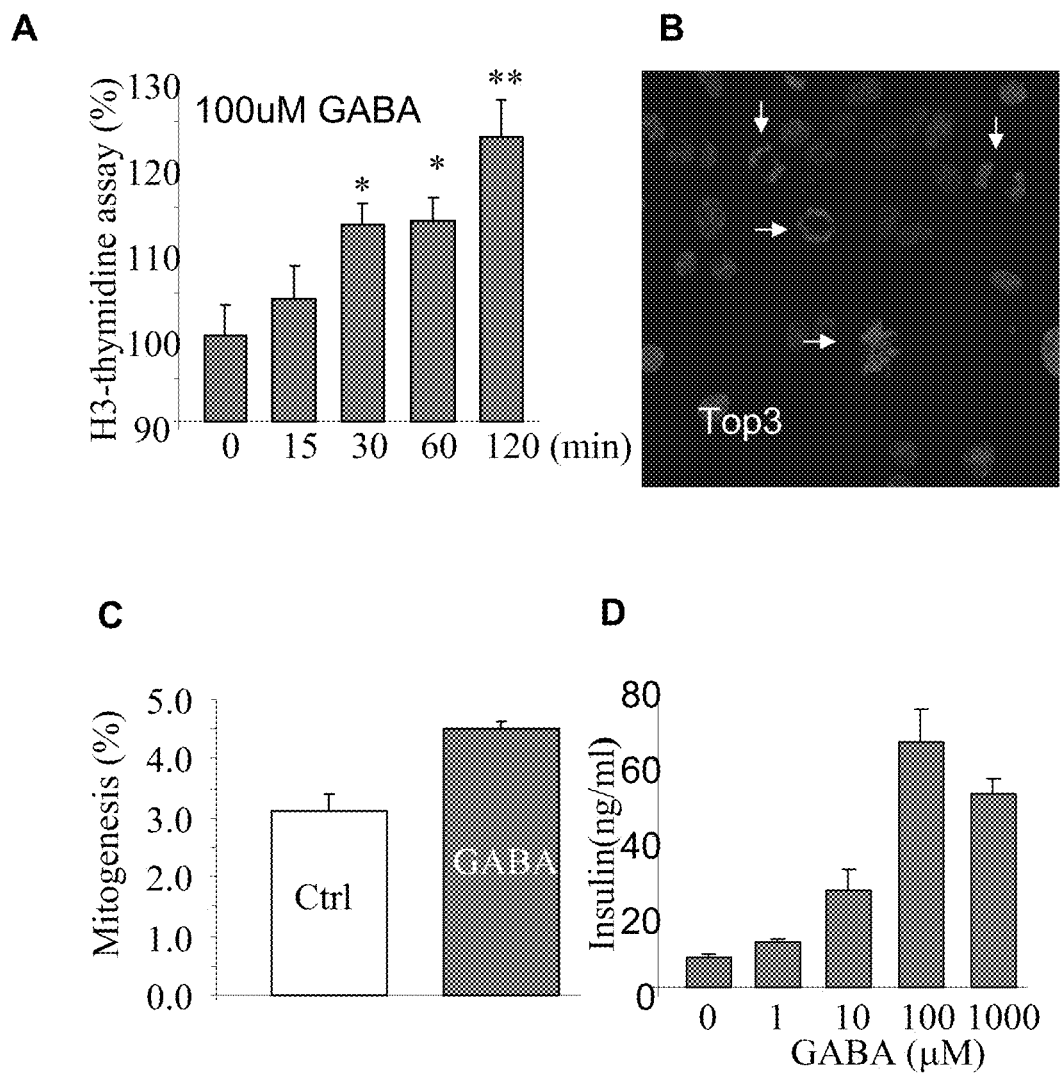
FIG. 10 A-D show GABA stimulates beta-cell proliferation. Treatment of GABA (100 mM) increased the $^3$H-thymidine incorporation into the insulin-secreting INS-1 cells in a time-dependent manner (A). A nuclear staining of INS-1 cells is shown (B) and the arrows indicate the cells are undergoing mitogenesis. The bar graphs represent the counting results of the dividing cells from GABA-treated or saline (Ctrl) treated cells (C). GABA also dose-dependently increases insulin secretion from INS-1 cells (D).

These in vivo animal studies clearly demonstrated that preventive and therapeutic effects of GABA may be potentially exerted by two arms: autoimmune regulation (i.e. specifically suppressing the diabetogenic T-cells) and proliferation and regeneration of islet beta cells. To verify if GABA indeed promote the beta-cells growth, in vitro assays were performed in insulin-secreting beta-cells INS-1. As shown GABA, dose-dependently increased INS-1 cell proliferation as exemplified by the $^3$H-thymidine incorporation assay (FIG. 10A). These findings were consistent to the results from separated cell mitogenic assay (FIG. 10B, 10C). Furthermore, GABA stimulated insulin secretion from the INS-1 beta cells in a dose dependent fashion (FIG. 10D). These in vitro data are consistent with the in vivo findings of embodiment of the disclosure that GABA promoted islet beta cell mass expansion and prevented and reversed diabetes in T1D diabetes models. The potential o GABA in promoting beta-cell growth is also existent in prior art (Ligon B et al, 2007 Diabetologia 50(4):764-73).

Figure 11:
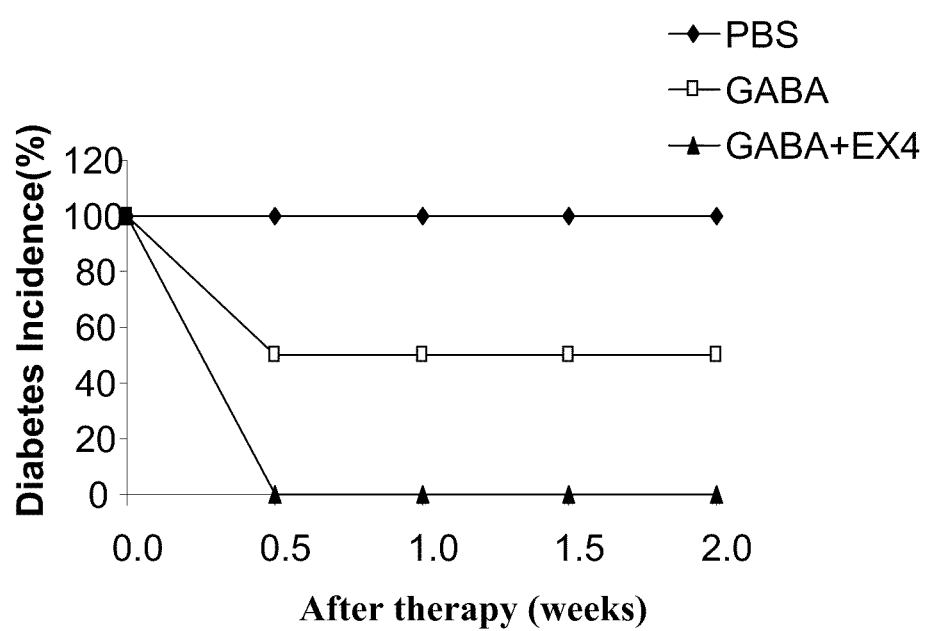
FIG. 11. Incidence of diabetes is significantly lower in established diabetic NOD mice which received GABA treatment or a combined therapy of GABA (20 □g mouse) and Ex4 (1 nmol/kg). The diabetes incidence is considered when the blood glucose is ≥12 mM and the treatment was then initiated from this point. The therapies are PBS, GABA alone and GABA plus Ex4.

As the demonstration of that treatment of GABA alone is not able to achieve a full remission in NOD mice after the onset of diabetic hyperglycemia. And, given that most patients at the time of diagnosis more than 70% islet beta-cells have been destroyed (Cnop M et al, 2005 Diabetes 54 Suppl 2:S97-107), it appears that a strategy that involves in suppression of islet autoimmunity alone may not be sufficient to fully reverse the diabetes. I propose to develop a combined therapy strategy involving synergic beta-cell regeneration and autoimmune suppression, in order to achieve a full remission of diabetes in a subject. As shown, a combined therapy with daily injections of GABA and GLP-1/Ex4 in established diabetes showed remarkable improved efficacy in which the diabetes incidence was significantly lower than GABA treatment alone (FIG. 11). Therefore, the co-administration of GABA and GLP-1/Ex4 completely reverses diabetes in the established diabetes in NOD mice (determined at two weeks after treatment).

The advantage of this combined therapy is obvious compared with GABA therapy alone (FIG. 7A, FIG. 11) or GLP-1/Ex4 therapy alone in the NOD mice (Hadjiyanni I et al, 2008 Endocrinology. 149(3):1338-49). The dramatically improved efficacy from the combined therapy may not just be a result of the superposition effect of GABA or GLP-1/Ex4, as previous demonstration that effects GLP-1/Ex4 on modulation of diabetes onset in NOD mice are marginal (Hadjiyanni I et al, 2008 Endocrinology. 149(3):1338-49). Potentially, the synergic efficacy of GABA and GLP-1/Ex4 could achieve a reciprocity effect which is exemplified by the further experimentation shown in FIG. 12 and FIG. 13. In these in vitro assays using GLP-1-secreting and/or insulin-secreting cells, it was shown that the production and secretion of GLP-1 in the gut-derived cells (STC-1) were modulated by GABA, and the production and release of GABA from the beta-cells were also modulated by GLP-1. The specificity of these assays was determined by including the $GABA_AR$ antagonists or GLP-1 receptor antagonist in the assays. Such modulation of GLP1/Ex4 on GABA production and release was shown in a time- and dose-dependent manner. Blockage of the GLP-1 receptor in the beta-cells attenuated the action of GLP-1/Ex4 on GABA production and release, indicating that the effects of GLP1/Ex4 on GABA production and secretion in the beta-cells are mediated by the activation of GLP-1 receptors in the beta-cells. The reciprocity effect of GABA and GLP-1/Ex4 as demonstrated in these in vitro assays may provide an in vivo mechanism by which GABA and GLP-1/Ex4 simultaneously act on the respective target and thus yield an "positive-feedback-loop" like efficacy.

Description of the Experimental Techniques

The techniques used for the in vivo and in vitro studies in this embodiment of the disclosure are also described. CD1 mice (Charles River Laboratories, St Constant, Canada), NOD mice and transgenic TCR NOD mice (Jackson Laboratory, USA) were housed under a controlled temperature and a 12-h light/12-h dark cycle in the St. Michael's Hospital Animal facility with free access to food (normal rodent chow) and water, except where noted. All procedures were conducted according to protocols and guidelines approved by the Canadian Council of Animal Care and the St. Michael's Hospital Animal Care committee. Mice were treated with GABA by daily intraperitoneal (i.p.) injection of 20 g GABA per mouse to reach ~200 µM circulation concentration and PBS as control. The daily treatment is continuously conducted during 60-day experimental period. One wk after the GABA and PBS treatment, diabetes was induced in both groups by i.p.-injection of low-dose streptozotocin (STZ, Sigma Chemical Co., St. Louis, Mo. 40 mg/kg body weight) for 5 consecutive days. The development of hyperglycemia was monitored by measuring blood glucose from the tail vein every third day following STZ injections using an Ascensia ELITE® XL glucose meter. For some studies, overtly diabetic mice induced by STZ and without GABA treatment were divided into two groups: one group started receiving daily i.p. injection of 20 g GABA whereas other group received only PBS. The treatment was continued for 75 days. The handling of the NOD mice were similar to those CD1 mice except the STZ injection. The NOD mice have a susceptibility to spontaneous development of autoimmmune T1D. The TCR transgenic 8.3-NOD mice have a markedly accelerated disease (J. Vergdaguer et al, 1997 J Exp Med. 186(10):1663-76).

Intra-Peritoneal Glucose Tolerance Test:

Groups of mice were subject to a glucose tolerance test (IPGTT) before treatment (day 0), one, three, and five weeks after administration and the day prior termination. For IPGTT, mice were fasted overnight for 15 h, and were given 1.5 g glucose/kg body weight via i.p.-injection. Blood was drawn from the tail vein and blood glucose was measured at 0, 10, 20, 30, 60, 90, and 120 min after glucose administration.

Insulin, Glucagon Tolerance Assays:

Insulin tolerance test (ITT) was performed in non-fasting mice by i.p.-injection of 2.5 unit insulin/kg body weight. Blood was drawn from the tail vein and blood glucose levels were measured at 0, 20, 30, 40, 60, 90, and 120 min after insulin administration. Glucagon tolerance test (GTT) was performed in 15 hrs fasted mice: glucagon were i.p.-injected (50 ng/g body weight) and blood was drawn from the tail vein and blood glucose levels were measured at 0, 10, 20, 30, 60, 90, and 120 min after glucagon administration.

Metabolic Studies:

Mice were housed in metabolic cages prior to initiation of GABA and PBS treatment and before termination of experiments. Food intake, water consumption and urine output were measured. To determine the fat distribution, three intra-abdominal fat pads retroperitoneal, mesenteric and epididymal were dissected and weighed. Subcutaneus fat was also analyzed.

Biochemical Analysis:

Blood samples (200 µL) were collected from the saphenous vein at time as indicated and at the termination of experiments via cardiac puncture (1 mL) for measurement of insulin, glucagon, and cytokine profiles. Serum was collected by centrifugation and stored at −80° C. until use. Insulin and glucagon concentration in serum samples were determined using insulin ELISA kit (Crystal Chem., Chicago, Ill., USA) and glucagon RIA kit (Linco Research, St. Louis, Miss., USA). Circulating GLP-1 levels were determined using GLP-1 RIA kit (Linco Research, St. Louis, Miss., USA). Cytokine concentration in the serum samples was determined using kit Multiplex Bead-based Cytokine assay (BioRed, Canada).

Pancreas Harvesting and Tissue Processing:

Pancreas harvesting and tissue processing were performed as described previously (Wang Q, Brubaker P L 2002 Diabetologia. 45(9):1263-73.). Briefly, after cardiac puncture under anesthesia, a midlaparotomy was performed and the pancreas was immediately dissected from surrounding tissues, cleared of fat and lymph nodes, blotted, weighed, and placed in a formaldehyde-acetic acid solution. The procedure from completion of cardiac puncture to placement of tissue in fixative was completed within 5 min. After overnight fixation, the pancreas was washed in cold running water, cut into 10-12 segments. Following a throughout dehydration in ethanol and xylene, all of the segments from a single pancreas were embedded into one paraffin block and sectioned at 5-µm thickness using the Leica RM2145 semi-motorized rotary microtome (Leica Microsystems, Nussloch, Germany). This permits analysis of the entire pancreas in a single section.

The Beta-Cell and Alpha-Cell Mass Measurement:

Following dewaxing, dehydration as described previously (Wang Q, Brubaker P L 2002 Diabetologia 45:1263-1273), endogenous peroxidase activity was quenched by incubating sections in 0.3% $H_2O_2$ in water for 30 min and antigen retrieval was performed by heating slides in 10 mM sodium citrate buffer, pH 6.0, at ~70° C. for 30 min. After blocking non-specific binding sites with 10% normal goat serum in PBS, tissue sections were incubated overnight at 4° C. with polyclonal guinea pig anti-insulin (1:1000; DAKO Corporation, Corpinteria, Calif.) for insulin staining and with rabbit anti-human glucagon (1:800; DAKO) at room temperature for 2 hr for glucagon staining. After 5-min wash with PBS, sections were incubated with biotinylated mouse anti-guinea pig IgG (1:500; Vector Laboratories Inc., Burlingame, Calif.) and biotinylated rat anti-Rb IgG (1:500; Vector Laboratories Inc.) for 1 hr at room temperature. After a 5-min wash with PBS, the sections were incubated with an avidin-biotin complex (VECTASTATIN ABC kit; Vector Laboratories, Inc.) for 30 min at room temperature before developing in DAB (Vector Laboratories Inc.) and counterstaining in Hematoxylin and Eosin (H & E). The slides were visualized using ScanScope CS (Aperio technologies, Vista, Calif.) and analyzed using ImageScope program (Aperio technologies). Entire pancreatic tissue areas were outlined and the numbers of strong positive signals (Nsp) within those areas, representing insulin or glucagon staining, were detected by the Positive Pixel Count Algorithm (Aperio technologies). This algorithm was also used to detect the total number of positive and negative signals (NTotal), which represents the total pancreatic tissue area. Total beta-cell mass for each pancreas was determined as the product of the total cross-sectional beta-cell area (Nsp) over total tissue area (NTotal) and the weight of the pancreas before fixation.

Detection of Beta-Cell Apoptosis:

Apoptosis of pancreatic islet beta-cells was evaluated by caspase-3 staining (Cell Signaling). Caspase-3 is a commonly used apoptosis marker of islet beta-cells (Cnop M et al, 2005 Diabetes. 54 Suppl 2:S97-107 To identify the islet beta-cells, double immunostained for insulin was performed as described above. The 4'-6-diamidino-2-phenylindole (DAPI) was used for nuclear staining, and using the quantitative terminal deoxynucleotidyl transferase biotindUTP nick end labelling (TUNEL) using the In Situ Cell Death Detection Kit, TMR Red (Roche Diagnostics, Mannheim, Germany) in paraffin-embedded pancreatic sections. For the DAPI analysis, the pancreatic sections pre-stained with mouse anti-insulin IgG (1:1000) and Cy3-conjugated anti-mouse IgG (1:500) were incubated with DAPI (1 μg/ml in PBS, 5 min, Sigma, Missouri, USA). The apoptotic beta-cells were identified by the typical morphologic criteria of chromatin condensation and fragmentation (Finegood D T, et al, 2001 Diabetes 50:1021-1029). For the TUNEL assay, the pancreatic sections pre-stained with guinea-pig anti-insulin IgG (1:1,000, Dako-Cytomation, Mississauga, ON, Canada) and FITC-conjugated secondary antibodies were incubated with the tunnel reaction mixture (60 min, RT, in dark). The pancreatic sections were incubated with DAPI prior to visualization using confocal microscopy (Zeiss LSM 510).

Cell Proliferation Assay by $^3$H-Thymidine Incorporation:

INS-1 cells were grown to 80-85% confluence in 12-well plates, serum-starved for 24 h and then treated with GABA at various concentrations in the presence of 3 mmol/l glucose. Some cells were also pre-incubated with GABA receptor antagonist for 20 h prior before the treatment. DNA synthesis was measured by incubating cells with 37 kBq/ml 3H-methylthymidine (specific activity: 3000 GBq/mmol; Amersham Pharmacia Biotech) for 4 h. Cells were then washed twice in ice-cold PBS and incubated for 30 min in 1 ml of 5% trichloroacetic acid on ice to precipitate the DNA. The liquid layer was removed by aspiration and 250 μl of 0.1 mol/l sodium hydroxide was added to the cells for 30 min at room temperature. During this time the container was gently shaken. The solubilised material was then transferred to 5 ml of scintillant, and radioactive counts were determined by liquid scintillation counting.

Flow Cytometry Analysis:

FITC- or PE-labeled rat anti-mouse CD4, CD25, CD 86 (B7.1), CD152 (CTLA-4), and isotype IgG were from BD Pharmingen. Non-labeled and biotinylated mouse anti-human/mouse LAP-TGFbeta were from R&D Systems. Rabbit anti-rat/mouse neuropilin1 (Nrp1) polyclonal IgG was purchased from Oncogene. Anti-LAP-TGFbeta and mouse isotype IgG were labeled with Alexa Fluor 488 (Molecular Probes) according to the manufacturer's protocol. Anti-Nrp1 IgG and rabbit normal IgG were labeled with Alexa Fluor 647. Because anti-Nrp1 antibodies contain 0.2% gelatin, swine gelatin was also labeled with Alexa Fluor 647, and this preparation was added to the isotype antibodies to the final 0.2% to correct for possible binding of labeled gelatin, a modified extracellular matrix protein, to lymphocytes.

In Vitro Spleen Cell Stimulation, Proliferation, and Cytokine Assays:

the spleen cells isolated from saline-treated or GABA-treated TCR NOD mice were plated in serum-free chemically defined medium AIM V (Invitrogen Canada, Burlington, ON), supplemented with 0.05 mM 2-mercaptoethanol. Antigen peptide s were added to the culture medium at a final concentration of 0.05 mg/ml. An equimolar mixture of three GAD65 synthetic peptides (Sheldon Biotechnology Centre, McGill University) was prepared. These peptides were: TYE-IAPVFVLLEYVTLKKMREIIGWPGGSGD (amino acids 206-236 of SEQ ID NO:6); AALGIGTDSVILIKCDERGK (amino acids 290-309 of SEQ ID NO:6); and VPPSLRTLED-NEERMSRLSKVAPVIKARMMEYGTT (amino acids 509-543 of SEQ ID NO:6). These peptide fragments cover most of the antigen determinants recognized by T cells, as summarized in (Nauck M A, et al, 1993 J Clin Invest 91:301-307). Bovine insulin was purchased from Sigma Chemicals, MO. Endotoxin-free bovine serum albumin (BSA) was from Calbiochem (San Diego, Calif.). Endotoxin-free ovalbumin (OVA) was purified from fresh chicken eggs as described in (Kieffer T J, et al, 1995 Endocrinology 136:3585-3596), and added to cultures at a concentration of 0.05 mg/ml. In preliminary tests, this OVA preparation did not affect proliferation of naïve T cells. Proliferation was determined with the MTT assay as described (Mentlein R, et al, 1993 Eur J Biochem 214:829-835), based on the accumulation of formazan (the product of MTT reduction). In brief, MTT solution was added to the cells in 96 well plate after 72 h of antigen stimulation in a final concentration of 1 mg/ml. The assay was performed in quadruplicates. After 4 h, the reaction was stopped with isopropanol, acidified with 0.04 M HCl. Antigen-stimulated proliferation was measured as the increase in optical density (OD) at 540 nm induced by addition of antigen to the cells. In mixed cell assays where suppression was observed, the percent suppression of antigen-stimulated proliferative responses was calculated as follows:

cAMP Determination:

cAMP determination is a method that can evaluate the G-protein coupled receptor (GPCR) activation (Lee et al., 2000 Biochim Biophys Acta. 1490(3):311-323). Intracellular cAMP levels were determined in isolated islet cells or cultured insulin-secreting cells cultured in 35 mm$^2$ dishes. They were preincubated in the buffer containing 130 mM NaCl, 5 mM KCl, 1 mM sodium phosphate, 1 mM MgSO4, 2 mM CaCl$_2$, 20 mM HEPES buffer (pH 7.4), 6 mm glucose, and 0.1% BSA (RIA grade, Sigma) for 1 h. The PKA inhibitors were added for 20 min, and isobutyl methylxanthine (100 μM) for 10 min before addition of the compound for 20 min. Cells were washed three times in ice-cold PBS, cAMP extracted with hydrochloric acid (0.1M, 300 μl) and measured as per the cAMP RIAs (Biomedical Technologies, Stoughton, Mass.).

PI 3-Kinase Activity Assay:

PI3-kinase is upstream of Akt (Wang et al., 1999 Mol Cell Biol. 19(6):4008-4018). Whole cell lysates were obtained from isolated islet cells and insulin-secreting cell line (eg INS-1 cells and beta TC cells) pre-treated with the composition of sn embodiment of the disclosure for 20 min, and PI 3-kinase was immunoprecipitated using an antibody against the p85-regulatory subunit of PI 3-kinase (Santa Cruz Biotechnology). Activity was detected and quantified by measuring the formation of [$^{32}$P]PI 3-phosphate (Wang et al., 1998 Biochem J. 331(Pt 3):917-928). Briefly, after overnight incubation with the antibody-coated beads, the bound protein was washed three times with buffer I (PBS containing 1% Nonidet P-40 and 100 μM Na$_3$VO$_4$), three times with buffer II (100 mM Tris-HCl (pH 7.5), 500 mM LiCl, and 100 μM Na$_3$VO$_4$), and finally three times with buffer III (Tris-HCl (pH 7.5), 100 mM NaCl, 1 mM EDTA and 100 μM Na$_3$VO$_4$). After washing, immunoprecipitates are resuspended in 50 μl buffer III with the addition of 10 μl 100 mM MgCl$_2$ and 10 μl PI (2 μg/ml). The samples sat at room temperature for 5 min before the addition of 10 μl ATP (ATP 440 μM with 30 μCi/10 μl [$^{32}$P]ATP). The samples were then shaken at room temperature for 10 min. The reaction was stopped by the addition of 20 μl 8 N HCl and 160 μl chloroform-methanol (1:1). The lipids were extracted by standard methods, dried down, resuspended in 20 µl chloroform-methanol (1:1), were separated on thin layer silica gel plates (pretreated with 10% w/v potassium oxalate) in a solvent system of chloroform-methanol-water-$NH_4OH$ (60:47:11:2.2, vol/vol/vol/vol). Incorporation of $^{32}P$ into PI 3-phosphate is detected by autoradiography, and activity was quantified using a Molecular Dynamics PhosphorImager System (Sunnyvale, Calif.).

Akt Kinase Assays:

After treatment with the composition of sn embodiment of the disclosure for 10 min, whole cell lysates were obtained from isolated islet cells and insulin-secreting cell line (eg INS-1 cells and beta TC cells), using lysis buffer containing 50 mM HEPES (pH 7.6), 150 mM NaCl, 10% (vol/vol) glycerol, 1% (vol/vol) Triton X-100, 30 mM sodium pyrophosphate, 10 mM NaF, 1 mM EDTA, 1 mM phenylmethylsulfonyl fluoride, 1 mM benzamidine, 1 mM $Na_3VO_4$, 1 mM dithiothreitol [DTT], and 100 nM okadaic acid (Wang et al., Mol Cell Biol. 1999; 19(6):4008-4018). Akt antibody is precoupled (16 hours) to a mixture of protein A- and protein G-Sepharose beads. These antibody-bead complexes are washed twice with phosphate-buffered saline (PBS) and once with lysis buffer (4° C.). Akt is immunoprecipitated by incubating 200 µg of total cellular protein with the anti-Akt-bead complexes for 2 to 3 h with constant rotation (4° C.). Akt immunocomplexes were washed four times with 1 ml of wash buffer (25 mM HEPES [pH 7.8], 10% [vol/vol] glycerol, 1% [vol/vol] Triton X-100, 0.1% [wt/vol] bovine serum albumin, 1 M NaCl, 1 mM DTT, 1 mM phenylmethylsulfonyl fluoride, 1 mM microcystin, and 100 nM okadaic acid) and twice with 1 ml of kinase buffer (50 mM Tris-HCl [pH 7.5], 10 mM $MgCl_2$, and 1 mM DTT). The immunocomplexes were incubated with constant agitation for 30 minutes at 30° C. with 30 µL of reaction mixture (kinase buffer containing 5 µM ATP, 2 µCi of [γ-$^{32}P$]ATP, and 100 µM Crosstide). Following the reaction, 30 µl of the supernatant was transferred onto Whatman p81 filter paper and washed four times for 10 minutes each time with 3 ml of 175 mM phosphoric acid and once with distilled water for 5 min. The filters were air dried and then subjected to liquid scintillation counting.

MAP Kinase Assay:

After 20 min treatment with the composition of an embodiment of the disclosure, beta-cells were labeled with 1.25 microcurie $^{32}Pi$/group (NEN Life Science Products, Boston, Mass.) in phosphate-free RPMI medium without serum for 3 h at 37° C. The cells were harvested and placed in RPMI with 100 ng/ml LBP (PS-binding protein) and treated with the compositions of an embodiment of the disclosure for 30 min. After the incubation with the composition of an embodiment of the disclosure, the cells were stimulated with LPS for 15 min at 37° C. The cells were harvested, resuspended in lysis buffer (1% Nonidet P-40, 1% sodium deoxycholate, 0.1% SDS, 0.15 M NaCl, 0.01 M Na3PO4 (pH 7.2), 2 mM $Na_3VO_4$, 1 µM okadaic acid, 100 µg/ml PMSF, 50 µg/ml aprotinin, 10 µg/ml leupeptin, and 50 µg/ml pepstatin, all from Boehringer Mannheim), and sonicated. MEK was immunoprecipitated from the lysate, and the sample separated on a 10% SDS-PAGE discontinuous gel, and immuoblotting was performed using anti-phosphor-MEK antibody (Oncogene Research Products, San Diego, Calif.).

Quantitation of GABA:

The Free Amino Acid Analysis was performed on a Waters Acquity HPLC System. The Waters Acquity HPLC system employed consists of a Binary Solvent Manager, a Sample Manager, a TUV Detector and a Waters Acquity HPLC BEH C18 column (2.1×100 mm). Data was collected, stored and processed using Waters Empower 2 Chromatography software. Drying was done using a Tomy CC-181 Centrifugal Concentrator with a Sargent-Welch Model 8821 Vacuum pump. The operational procedures are as following: an aliquot of the sample was transferred into a 6×55 mm glass culture tube and dried under vacuum using a centrifugal evaporator. After drying, the sample was treated with a redrying solution consisting of methanol:water:triethylamine (2:2:1), vortex-mixed and dried under vacuum for 15 minutes. Then the sample was derivatized for 20 minutes at room temperature with a derivatizing solution made up of methanol:water:triethylamine:phenylisothiocyanate (PITC) (7:1:1:1). After 20 minutes, the derivatizing solution was removed under vacuum for 15 minutes. Then the derivatized sample was again washed with the redrying solution, vortex-mixed and dried under vacuum for 15 minutes. The derivatized sample was dissolved in a given amount of sample diluent (pH 7.40) and an aliquot injected into the column, running on a modified PICO-TAG gradient. Column temperature was at 48 C. The derivatized amino acids were detected at 254 nm.

Statistical Analysis:

All data are presented as mean±SEM. Statistic analysis was performed using Student's t-test or analysis of variance (ANOVA) with 'n−1' post hoc custom hypotheses tests, as appropriate, with the SAS software (Statistical Analysis Systems, Cary, N.C.) or the GraphPad Prism 3.0 program (GraphPad Software Inc., San Diego, Calif.). The incidence of diabetes was plotted using the Kaplan-Meier method and statistical comparisons made with the log-rank test. The significance of differences in insulitis scores was determined with the Chi-squared test. The differences between groups in the in vitro proliferation and cytokine release assays were determined by analysis of variance (ANOVA). Significance was assumed at $p<0.05$.

Example 2

Effects of GABA on stimulation of GLP-1 secretion from gut-derived cell lines. The production and secretion of GLP-1 in the gut-derived cells (STC-1) are examined by GLP-1 RIA. The time and dose dependent effects of GABA on GLP-1 production and secretion are examined in the gut cell lines in the presence of various concentration of GABA in which the specificity is determined by including the $GABA_AR$ antagonists in the assay.

Effects of Ex4 on secretion and production of GABA in insulin-secreting beta-cells. GABA concentrations were determined by the Free Amino Acid Analysis. This was performed on a Waters Acquity HPLC System. INS-1 cells were grown in a 12-well plate. After overnight starvation in a serum-free medium, the cells were incubated with or without GLP-1, Ex4 (7-39) in the presence or absence of Ex9 (9-39) for various time points including 0, 2, 24 hrs. The specificity of the action of GLP-1 on GABA production and release is verified by including the assay the using Ex9 (9-39), a peptide known as a GLP-1 receptor antagonist.

It will be appreciated that the description above relates to the preferred embodiments by way of example only. Many variations on the composition and methods for delivering an embodiment of the disclosure will be obvious to those knowledgeable in the field, and such obvious variations are within the scope of an embodiment of the disclosure as described and claimed, whether or not expressly described.

TABLE 1

The molecular and structure of GABA and sequences of GLP-1 and/or Ex4, glucagon GIP, insulin GAD65, and others are as follows:

GABA molecular formula: $C_4H_9NO_2$; Molecular Weight: 103.12 g/mol.

molecular structure:

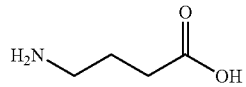

Human GLP-1
HAEGTFTSDV SSYLEGQAAK EFIAWLVKGR-$NH_2$
(SEQ ID NO:1)

Ex4
HGEGTFTSDL SKQMEEEAVR LFIEWLKNGG PSSGAPPPS-$NH_2$
(SEQ ID NO:2)

Human glucagon
HSQGTFTSDYSKYLDSRRAQDFVQWLMNT
(SEQ ID NO:3)

Human GIP
YAEGTFISDYSIAMDKIHQQDFVNWLLAQKGKKNDWKHNITQ
(SEQ ID NO:4)

Human insulin
MALWMRLLPLLALLALWGPDPAAAFVNQHLCGSHLVEALYLVCGERGFFYTPKTR
REAEDLQVGQVELGGGPGAGSLQPLALEGSLQKRGIVEQCCTSICSLYQLENYCN
(SEQ ID NO:5)

Human GAD65
```
  1 maspgsgfws fgsedgsgds enpgtarawc qvaqkftggi gnklcallyg daekpaesgg
 61 sqppraaark aacacdqkpc scskvdvnya flhatdllpa cdgerptlaf lqdvmnillq
121 yvvksfdrst kvidfhypne llqeynwela dqpqnleeil mhcqttlkya iktghpryfn
181 qlstgldmvg laadwltsta ntnmftyeia pvfvlleyvt lkkmreiigw pggsgdgifs
241 pggaisnmya mmiarfkmfp evkekgmaal prliaftseh shfslkkgaa algigtdsvi
301 likcdergkm ipsdlerril eakqkgfvpf lvsatagttv ygafdpllav adickkykiw
361 mhvdglmqnc nqmhasylfq qdkhydlsyd tgdkalqcgr hvdvfklwlm wrakgttgfe
421 ahvdkclela eylyniiknr egyemvfdgk pqhtnvcfwy ippslrtled neermsrlsk
481 vapvikarmm eygttmvsyq plgdkvnffr mvisnpaath qdidflieei erlgqdl
```
(SEQ ID NO:6)

Human GAD67
```
  1 masstpsssa tssnagadpn ttnlrpttyd twcgvahgct rklglkicgf lqrtnsleek
 61 srlvsafker qssknhlsce nsdrdarfrr tetdfsnlfa rdllpaknge eqtvqfllev
121 vdillnyvrk tfdrstkvld fhhphqlleg megfnlelsd hpesleqilv dcrdtlkygv
181 rtghprffnq lstgldiigl agewltstan tnmftyeiap vfvlmeqitl kkmreivgws
241 skdgdgifsp ggaisnmysi maarykyfpe vktkgmaavp klvlftseqs hysikkagaa
301 lgfgtdnvil ikcnergkii padfeakile akqkgyvpfy vnatagttvy gafdpiqeia
361 dicekynlwi hvdaawgggl lmsrkhrhkl ngieransvt wnphkmmgvl lqcsailvke
421 kgilqgcnqm cagyllqpdk qydvsydtgd kaiqcgrhvd ifkfwlmwka kgtvgfenqi
481 nkclelaeyl yakiknreef emvfngepeh tsvcfwyipq slrgvpdspq rreklhkvap
541 kikalmmesg ttmvgyqpqg dkanffrmvi snpaatqsdi dflieeierl gqdl
```
(SEQ ID NO:7)

Human Akt/Protein kinase B:
```
  1 mkterprpnt fiirclqwtt viertfhvet peereewtta iqtvadglkk qeeeemdfrs
 61 gspsdnsgae emevslakpk hrvtmnefey lkllgkgtfg kvilvkekat ayyamkilkk
121 evivakdeva htltenrvqq nsrhpfltrl kysfqthdrl cfvmeyangg elffhlsrer
181 vfaedrarfy gaeivsaldy lhseknvvyr dikienimid kdghikitdf glckegikdg
241 atmktfcgtp eylapevled ndygravdww glgvvmyemm cgrlpfynqd hekifeijim
301 eeirfprtlg peaksllsgl lkkdpkqrlg ggsedakeim qhrfftgivw qhvyekklsp
361 pfkpqvtset dtryfdeeft aqmititppd qddsmecvds errphfpqfs yspsata
```
(SEQ ID NO:8)

Human MAP kinase:
```
  1 msdskcdsqf ysvqvadstf tvlkryqqlk pigsgaqgiv caafdtvlgi nvavkklsrp
 61 fqnqthakra yrelvllkcv nhkniislln vftpqktlee fqdvylvmel mdanlcqvih
121 meldhermsy llyqmlcgik hlhsagiihr dlkpsnivvk sdctlkildf glartactnf
181 mmtpyvvtry yrapevilgm gykenvdiws vgcimgelvk gcvifqgtdh idqwnkvieq
241 lgtpsaefmk klqptvrnyv enrpkypgik feelfpdwif pseserdkik tsqardllsk
301 mlvidpdkri svdealrhpy itvwydpaea eapppqiyda qleerehaie ewkeliykev
361 mdweerskng vvkdqpsdaa vssnatpsqs ssindissms teqtlasdtd ssldastgpl
421 egcr
```
(SEQ ID NO:9)

TABLE 1-continued

The molecular and structure of GABA and sequences of GLP-1 and/or Ex4, glucagon GIP, insulin GAD65, and others are as follows:

Human caspase-3:
```
  1 mentensvds ksiknlepki ihgsesmdsg mswdtgykmd ypemglciii nnknfhkstg
 61 mtsrsgtdvd aanlretfrn lkyevrnknd ltreeivelm rdvskedhsk rssfvcvlls
121 hgeegiifgt ngpvdlkkit nffrgdrcrs ltgkpklfii qacrgteldc gietdsgvdd
181 dmachkipvd adflyaysta pgyyswrnsk dgswfiqslc amlkqyadkl efmhiltrvn
241 rkvatefesfsfdatfhakk qipcivsmlt kelyfyhi (SEQ ID NO:10)
```

The invention claimed is:

1. A method of ameliorating symptoms of type 1 diabetes (T1D), said method comprising administering a composition comprising an effective amount of:
   a. gamma-amino butyric acid (GABA) or a pharmaceutically acceptable salt thereof; and
   b. exendin-4 (Ex4) of SEQ ID NO:2.

2. The method at claim 1, wherein said composition is administered by a method selected from topical administration, oral administration, aerosol administration, intraperitoneal injection, intravenous injection and/or intramuscular injection.

3. The method of claim 1, wherein the dosage of the composition is 0.01-10 mmol of GABA per kg body weight and 0.02 to 1000 nmol of the Ex4 per kg body weight.

4. The method of claim 1, wherein the dosage of the composition is between about 0.002-2 mg of GABA per kg body weight and 0.2-1000 nmol of the Ex4 per kg body weight.

* * * * *

SEQUENCE LISTING

<160> NUMBER OF SEQ ID NOS: 10

<210> SEQ ID NO 1
<211> LENGTH: 30
<212> TYPE: PRT
<213> ORGANISM: Homo sapiens

<400> SEQUENCE: 1

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30
```

<210> SEQ ID NO 2
<211> LENGTH: 39
<212> TYPE: PRT
<213> ORGANISM: Heloderma suspectum

<400> SEQUENCE: 2

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

<210> SEQ ID NO 3
<211> LENGTH: 29
<212> TYPE: PRT
<213> ORGANISM: Homo sapiens

<400> SEQUENCE: 3

```
His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25
```

<210> SEQ ID NO 4
<211> LENGTH: 42
<212> TYPE: PRT
<213> ORGANISM: Homo sapiens

<400> SEQUENCE: 4

```
Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40
```

<210> SEQ ID NO 5
<211> LENGTH: 110
<212> TYPE: PRT
<213> ORGANISM: Homo sapiens

<400> SEQUENCE: 5

```
Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110
```

<210> SEQ ID NO 6
<211> LENGTH: 537
<212> TYPE: PRT
<213> ORGANISM: Homo sapiens

<400> SEQUENCE: 6

```
Met Ala Ser Pro Gly Ser Gly Phe Trp Ser Phe Gly Ser Glu Asp Gly
1               5                   10                  15

Ser Gly Asp Ser Glu Asn Pro Gly Thr Ala Arg Ala Trp Cys Gln Val
            20                  25                  30

Ala Gln Lys Phe Thr Gly Gly Ile Gly Asn Lys Leu Cys Ala Leu Leu
        35                  40                  45

Tyr Gly Asp Ala Glu Lys Pro Ala Glu Ser Gly Gly Ser Gln Pro Pro
50                  55                  60

Arg Ala Ala Ala Arg Lys Ala Ala Cys Ala Cys Asp Gln Lys Pro Cys
65                  70                  75                  80

Ser Cys Ser Lys Val Asp Val Asn Tyr Ala Phe Leu His Ala Thr Asp
                85                  90                  95

Leu Leu Pro Ala Cys Asp Gly Glu Arg Pro Thr Leu Ala Phe Leu Gln
            100                 105                 110

Asp Val Met Asn Ile Leu Leu Gln Tyr Val Val Lys Ser Phe Asp Arg
        115                 120                 125

Ser Thr Lys Val Ile Asp Phe His Tyr Pro Asn Glu Leu Leu Gln Glu
130                 135                 140

Tyr Asn Trp Glu Leu Ala Asp Gln Pro Gln Asn Leu Glu Glu Ile Leu
145                 150                 155                 160

Met His Cys Gln Thr Thr Leu Lys Tyr Ala Ile Lys Thr Gly His Pro
                165                 170                 175

Arg Tyr Phe Asn Gln Leu Ser Thr Gly Leu Asp Met Val Gly Leu Ala
            180                 185                 190

Ala Asp Trp Leu Thr Ser Thr Ala Asn Thr Asn Met Phe Thr Tyr Glu
        195                 200                 205

Ile Ala Pro Val Phe Val Leu Leu Glu Tyr Val Thr Leu Lys Lys Met
210                 215                 220
```

```
Arg Glu Ile Ile Gly Trp Pro Gly Ser Gly Asp Gly Ile Phe Ser
225                 230                 235                 240

Pro Gly Gly Ala Ile Ser Asn Met Tyr Ala Met Met Ile Ala Arg Phe
            245                 250                 255

Lys Met Phe Pro Glu Val Lys Glu Lys Gly Met Ala Ala Leu Pro Arg
            260                 265                 270

Leu Ile Ala Phe Thr Ser Glu His Ser His Phe Ser Leu Lys Lys Gly
            275                 280                 285

Ala Ala Ala Leu Gly Ile Gly Thr Asp Ser Val Ile Leu Ile Lys Cys
            290                 295                 300

Asp Glu Arg Gly Lys Met Ile Pro Ser Asp Leu Glu Arg Arg Ile Leu
305                 310                 315                 320

Glu Ala Lys Gln Lys Gly Phe Val Pro Phe Leu Val Ser Ala Thr Ala
                325                 330                 335

Gly Thr Thr Val Tyr Gly Ala Phe Asp Pro Leu Leu Ala Val Ala Asp
            340                 345                 350

Ile Cys Lys Lys Tyr Lys Ile Trp Met His Val Asp Gly Leu Met Gln
            355                 360                 365

Asn Cys Asn Gln Met His Ala Ser Tyr Leu Phe Gln Gln Asp Lys His
370                 375                 380

Tyr Asp Leu Ser Tyr Asp Thr Gly Asp Lys Ala Leu Gln Cys Gly Arg
385                 390                 395                 400

His Val Asp Val Phe Lys Leu Trp Leu Met Trp Arg Ala Lys Gly Thr
                405                 410                 415

Thr Gly Phe Glu Ala His Val Asp Lys Cys Leu Glu Leu Ala Glu Tyr
            420                 425                 430

Leu Tyr Asn Ile Ile Lys Asn Arg Glu Gly Tyr Glu Met Val Phe Asp
            435                 440                 445

Gly Lys Pro Gln His Thr Asn Val Cys Phe Trp Tyr Ile Pro Pro Ser
            450                 455                 460

Leu Arg Thr Leu Glu Asp Asn Glu Glu Arg Met Ser Arg Leu Ser Lys
465                 470                 475                 480

Val Ala Pro Val Ile Lys Ala Arg Met Met Glu Tyr Gly Thr Thr Met
                485                 490                 495

Val Ser Tyr Gln Pro Leu Gly Asp Lys Val Asn Phe Phe Arg Met Val
            500                 505                 510

Ile Ser Asn Pro Ala Ala Thr His Gln Asp Ile Asp Phe Leu Ile Glu
            515                 520                 525

Glu Ile Glu Arg Leu Gly Gln Asp Leu
530                 535

<210> SEQ ID NO 7
<211> LENGTH: 594
<212> TYPE: PRT
<213> ORGANISM: Homo sapiens

<400> SEQUENCE: 7

Met Ala Ser Ser Thr Pro Ser Ser Ser Ala Thr Ser Ser Asn Ala Gly
1               5                   10                  15

Ala Asp Pro Asn Thr Thr Asn Leu Arg Pro Thr Thr Tyr Asp Thr Trp
            20                  25                  30

Cys Gly Val Ala His Gly Cys Thr Arg Lys Leu Gly Leu Lys Ile Cys
        35                  40                  45

Gly Phe Leu Gln Arg Thr Asn Ser Leu Glu Glu Lys Ser Arg Leu Val
    50                  55                  60
```

-continued

```
Ser Ala Phe Lys Glu Arg Gln Ser Ser Lys Asn Leu Leu Ser Cys Glu
 65                  70                  75                  80

Asn Ser Asp Arg Asp Ala Arg Phe Arg Thr Glu Thr Asp Phe Ser
             85                  90                  95

Asn Leu Phe Ala Arg Asp Leu Leu Pro Ala Lys Asn Gly Glu Glu Gln
            100                 105                 110

Thr Val Gln Phe Leu Leu Glu Val Val Asp Ile Leu Leu Asn Tyr Val
            115                 120                 125

Arg Lys Thr Phe Asp Arg Ser Thr Lys Val Leu Asp Phe His His Pro
            130                 135                 140

His Gln Leu Leu Glu Gly Met Glu Gly Phe Asn Leu Glu Leu Ser Asp
145                 150                 155                 160

His Pro Glu Ser Leu Glu Gln Ile Leu Val Asp Cys Arg Asp Thr Leu
            165                 170                 175

Lys Tyr Gly Val Arg Thr Gly His Pro Arg Phe Phe Asn Gln Leu Ser
            180                 185                 190

Thr Gly Leu Asp Ile Ile Gly Leu Ala Gly Glu Trp Leu Thr Ser Thr
            195                 200                 205

Ala Asn Thr Asn Met Phe Thr Tyr Glu Ile Ala Pro Val Phe Val Leu
210                 215                 220

Met Glu Gln Ile Thr Leu Lys Lys Met Arg Glu Ile Val Gly Trp Ser
225                 230                 235                 240

Ser Lys Asp Gly Asp Gly Ile Phe Ser Pro Gly Gly Ala Ile Ser Asn
            245                 250                 255

Met Tyr Ser Ile Met Ala Ala Arg Tyr Lys Tyr Phe Pro Glu Val Lys
            260                 265                 270

Thr Lys Gly Met Ala Ala Val Pro Lys Leu Val Leu Phe Thr Ser Glu
            275                 280                 285

Gln Ser His Tyr Ser Ile Lys Lys Ala Gly Ala Ala Leu Gly Phe Gly
            290                 295                 300

Thr Asp Asn Val Ile Leu Ile Lys Cys Asn Glu Arg Gly Lys Ile Ile
305                 310                 315                 320

Pro Ala Asp Phe Glu Ala Lys Ile Leu Glu Ala Lys Gln Lys Gly Tyr
            325                 330                 335

Val Pro Phe Tyr Val Asn Ala Thr Ala Gly Thr Thr Val Tyr Gly Ala
            340                 345                 350

Phe Asp Pro Ile Gln Glu Ile Ala Asp Ile Cys Glu Lys Tyr Asn Leu
            355                 360                 365

Trp Leu His Val Asp Ala Ala Trp Gly Gly Gly Leu Leu Met Ser Arg
            370                 375                 380

Lys His Arg His Lys Leu Asn Gly Ile Glu Arg Ala Asn Ser Val Thr
385                 390                 395                 400

Trp Asn Pro His Lys Met Met Gly Val Leu Leu Gln Cys Ser Ala Ile
            405                 410                 415

Leu Val Lys Glu Lys Gly Ile Leu Gln Gly Cys Asn Gln Met Cys Ala
            420                 425                 430

Gly Tyr Leu Leu Gln Pro Asp Lys Gln Tyr Asp Val Ser Tyr Asp Thr
            435                 440                 445

Gly Asp Lys Ala Ile Gln Cys Gly Arg His Val Asp Ile Phe Lys Phe
450                 455                 460

Trp Leu Met Trp Lys Ala Lys Gly Thr Val Gly Phe Glu Asn Gln Ile
465                 470                 475                 480

Asn Lys Cys Leu Glu Leu Ala Glu Tyr Leu Tyr Ala Lys Ile Lys Asn
            485                 490                 495
```

Arg Glu Glu Phe Glu Met Val Phe Asn Gly Glu Pro Glu His Thr Ser
                500                 505                 510

Val Cys Phe Trp Tyr Ile Pro Gln Ser Leu Arg Gly Val Pro Asp Ser
                515                 520                 525

Pro Gln Arg Arg Glu Lys Leu His Lys Val Ala Pro Lys Ile Lys Ala
                530                 535                 540

Leu Met Met Glu Ser Gly Thr Thr Met Val Gly Tyr Gln Pro Gln Gly
545                 550                 555                 560

Asp Lys Ala Asn Phe Phe Arg Met Val Ile Ser Asn Pro Ala Ala Thr
                565                 570                 575

Gln Ser Asp Ile Asp Phe Leu Ile Glu Glu Ile Glu Arg Leu Gly Gln
                580                 585                 590

Asp Leu

<210> SEQ ID NO 8
<211> LENGTH: 417
<212> TYPE: PRT
<213> ORGANISM: Homo sapiens

<400> SEQUENCE: 8

Met Lys Thr Glu Arg Pro Arg Pro Asn Thr Phe Ile Ile Arg Cys Leu
1               5                   10                  15

Gln Trp Thr Thr Val Ile Glu Arg Thr Phe His Val Glu Thr Pro Glu
                20                  25                  30

Glu Arg Glu Glu Trp Thr Thr Ala Ile Gln Thr Val Ala Asp Gly Leu
            35                  40                  45

Lys Lys Gln Glu Glu Glu Met Asp Phe Arg Ser Gly Ser Pro Ser
50                  55                  60

Asp Asn Ser Gly Ala Glu Glu Met Glu Val Ser Leu Ala Lys Pro Lys
65                  70                  75                  80

His Arg Val Thr Met Asn Glu Phe Glu Tyr Leu Lys Leu Leu Gly Lys
                85                  90                  95

Gly Thr Phe Gly Lys Val Ile Leu Val Lys Glu Lys Ala Thr Ala Tyr
            100                 105                 110

Tyr Ala Met Lys Ile Leu Lys Lys Glu Val Ile Val Ala Lys Asp Glu
        115                 120                 125

Val Ala His Thr Leu Thr Glu Asn Arg Val Gln Gln Asn Ser Arg His
    130                 135                 140

Pro Phe Leu Thr Arg Leu Lys Tyr Ser Phe Gln Thr His Asp Arg Leu
145                 150                 155                 160

Cys Phe Val Met Glu Tyr Ala Asn Gly Gly Glu Leu Phe Phe His Leu
                165                 170                 175

Ser Arg Glu Arg Val Phe Ala Glu Asp Arg Ala Arg Phe Tyr Gly Ala
            180                 185                 190

Glu Ile Val Ser Ala Leu Asp Tyr Leu His Ser Glu Lys Asn Val Val
        195                 200                 205

Tyr Arg Asp Leu Lys Leu Glu Asn Leu Met Leu Asp Lys Asp Gly His
    210                 215                 220

Ile Lys Ile Thr Asp Phe Gly Leu Cys Lys Glu Gly Ile Lys Asp Gly
225                 230                 235                 240

Ala Thr Met Lys Thr Phe Cys Gly Thr Pro Glu Tyr Leu Ala Pro Glu
                245                 250                 255

Val Leu Glu Asp Asn Asp Tyr Gly Arg Ala Val Asp Trp Trp Gly Leu
            260                 265                 270

```
Gly Val Val Met Tyr Glu Met Cys Gly Arg Leu Pro Phe Tyr Asn
            275                 280                 285

Gln Asp His Glu Lys Leu Phe Glu Leu Ile Leu Met Glu Glu Ile Arg
        290                 295                 300

Phe Pro Arg Thr Leu Gly Pro Glu Ala Lys Ser Leu Leu Ser Gly Leu
305                 310                 315                 320

Leu Lys Lys Asp Pro Lys Gln Arg Leu Gly Gly Gly Ser Glu Asp Ala
                325                 330                 335

Lys Glu Ile Met Gln His Arg Phe Phe Thr Gly Ile Val Trp Gln His
            340                 345                 350

Val Tyr Glu Lys Lys Leu Ser Pro Pro Phe Lys Pro Gln Val Thr Ser
        355                 360                 365

Glu Thr Asp Thr Arg Tyr Phe Asp Glu Glu Phe Thr Ala Gln Met Ile
370                 375                 380

Thr Ile Thr Pro Pro Asp Gln Asp Asp Ser Met Glu Cys Val Asp Ser
385                 390                 395                 400

Glu Arg Arg Pro His Phe Pro Gln Phe Ser Tyr Ser Pro Ser Ala Thr
                405                 410                 415

Ala

<210> SEQ ID NO 9
<211> LENGTH: 424
<212> TYPE: PRT
<213> ORGANISM: Homo sapiens

<400> SEQUENCE: 9

Met Ser Asp Ser Lys Cys Asp Ser Gln Phe Tyr Ser Val Gln Val Ala
1               5                   10                  15

Asp Ser Thr Phe Thr Val Leu Lys Arg Tyr Gln Gln Leu Lys Pro Ile
            20                  25                  30

Gly Ser Gly Ala Gln Gly Ile Val Cys Ala Ala Phe Asp Thr Val Leu
        35                  40                  45

Gly Ile Asn Val Ala Val Lys Lys Leu Ser Arg Pro Phe Gln Asn Gln
    50                  55                  60

Thr His Ala Lys Arg Ala Tyr Arg Glu Leu Val Leu Leu Lys Cys Val
65                  70                  75                  80

Asn His Lys Asn Ile Ile Ser Leu Leu Asn Val Phe Thr Pro Gln Lys
                85                  90                  95

Thr Leu Glu Glu Phe Gln Asp Val Tyr Leu Val Met Glu Leu Met Asp
            100                 105                 110

Ala Asn Leu Cys Gln Val Ile His Met Glu Leu Asp His Glu Arg Met
        115                 120                 125

Ser Tyr Leu Leu Tyr Gln Met Leu Cys Gly Ile Lys His Leu His Ser
    130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Cys Thr Asn Phe Met Met Thr Pro Tyr Val Val Thr Arg Tyr Tyr Arg
            180                 185                 190

Ala Pro Glu Val Ile Leu Gly Met Gly Tyr Lys Glu Asn Val Asp Ile
        195                 200                 205

Trp Ser Val Gly Cys Ile Met Gly Glu Leu Val Lys Gly Cys Val Ile
    210                 215                 220

Phe Gln Gly Thr Asp His Ile Asp Gln Trp Asn Lys Val Ile Glu Gln
```

```
                225                 230                 235                 240
Leu Gly Thr Pro Ser Ala Glu Phe Met Lys Lys Leu Gln Pro Thr Val
                    245                 250                 255
Arg Asn Tyr Val Glu Asn Arg Pro Lys Tyr Pro Gly Ile Lys Phe Glu
                    260                 265                 270
Glu Leu Phe Pro Asp Trp Ile Phe Pro Ser Glu Ser Glu Arg Asp Lys
                    275                 280                 285
Ile Lys Thr Ser Gln Ala Arg Asp Leu Leu Ser Lys Met Leu Val Ile
                290                 295                 300
Asp Pro Asp Lys Arg Ile Ser Val Asp Glu Ala Leu Arg His Pro Tyr
305                 310                 315                 320
Ile Thr Val Trp Tyr Asp Pro Ala Glu Ala Glu Ala Pro Pro Pro Gln
                    325                 330                 335
Ile Tyr Asp Ala Gln Leu Glu Glu Arg Glu His Ala Ile Glu Glu Trp
                    340                 345                 350
Lys Glu Leu Ile Tyr Lys Glu Val Met Asp Trp Glu Glu Arg Ser Lys
                    355                 360                 365
Asn Gly Val Val Lys Asp Gln Pro Ser Asp Ala Ala Val Ser Ser Asn
                370                 375                 380
Ala Thr Pro Ser Gln Ser Ser Ile Asn Asp Ile Ser Ser Met Ser
385                 390                 395                 400
Thr Glu Gln Thr Leu Ala Ser Asp Thr Asp Ser Ser Leu Asp Ala Ser
                    405                 410                 415
Thr Gly Pro Leu Glu Gly Cys Arg
                420

<210> SEQ ID NO 10
<211> LENGTH: 278
<212> TYPE: PRT
<213> ORGANISM: Homo sapiens

<400> SEQUENCE: 10

Met Glu Asn Thr Glu Asn Ser Val Asp Ser Lys Ser Ile Lys Asn Leu
1               5                   10                  15
Glu Pro Lys Ile Ile His Gly Ser Glu Ser Met Asp Ser Gly Met Ser
                20                  25                  30
Trp Asp Thr Gly Tyr Lys Met Asp Tyr Pro Glu Met Gly Leu Cys Ile
                35                  40                  45
Ile Ile Asn Asn Lys Asn Phe His Lys Ser Thr Gly Met Thr Ser Arg
            50                  55                  60
Ser Gly Thr Asp Val Asp Ala Ala Asn Leu Arg Glu Thr Phe Arg Asn
65                  70                  75                  80
Leu Lys Tyr Glu Val Arg Asn Lys Asn Asp Leu Thr Arg Glu Glu Ile
                85                  90                  95
Val Glu Leu Met Arg Asp Val Ser Lys Glu Asp His Ser Lys Arg Ser
                100                 105                 110
Ser Phe Val Cys Val Leu Leu Ser His Gly Glu Glu Gly Ile Ile Phe
            115                 120                 125
Gly Thr Asn Gly Pro Val Asp Leu Lys Lys Ile Thr Asn Phe Phe Arg
        130                 135                 140
Gly Asp Arg Cys Arg Ser Leu Thr Gly Lys Pro Lys Leu Phe Ile Ile
145                 150                 155                 160
Gln Ala Cys Arg Gly Thr Glu Leu Asp Cys Gly Ile Glu Thr Asp Ser
                165                 170                 175
Gly Val Asp Asp Asp Met Ala Cys His Lys Ile Pro Val Asp Ala Asp
```

-continued

```
                    180                 185                 190
Phe Leu Tyr Ala Tyr Ser Thr Ala Pro Gly Tyr Tyr Ser Trp Arg Asn
            195                 200                 205

Ser Lys Asp Gly Ser Trp Phe Ile Gln Ser Leu Cys Ala Met Leu Lys
        210                 215                 220

Gln Tyr Ala Asp Lys Leu Glu Phe Met His Ile Leu Thr Arg Val Asn
225                 230                 235                 240

Arg Lys Val Ala Thr Glu Phe Glu Ser Phe Ser Phe Asp Ala Thr Phe
                245                 250                 255

His Ala Lys Lys Gln Ile Pro Cys Ile Val Ser Met Leu Thr Lys Glu
            260                 265                 270

Leu Tyr Phe Tyr His Leu
        275
```